United States Patent
Luo et al.

(10) Patent No.: US 9,580,498 B2
(45) Date of Patent: Feb. 28, 2017

(54) MONOCLONAL ANTIBODY FOR ANTAGONIZING AND INHIBITING BINDING OF VASCULAR ENDOTHELIAL GROWTH FACTOR TO ITS RECEPTOR, AND CODING SEQUENCE

(71) Applicant: SUZHOU STAINWEI BIOTECH INC., Jiangsu (CN)

(72) Inventors: Shiping Luo, Jiangsu (CN); Hongqun Hu, Jiangsu (CN); Zui Chen, Jiangsu (CN); Mingwen Cai, Jiangsu (CN); Yanan Sun, Jiangsu (CN); Haiyun Liu, Jiangsu (CN); Jianying Zhou, Jiangsu (CN); Xiaoqi Song, Jiangsu (CN); Xiaoya Ping, Jiangsu (CN); Siyu Chen, Jiangsu (CN); Donghong Shi, Jiangsu (CN); Yiqing Xu, Jiangsu (CN); Qunmin Zhou, Jiangsu (CN)

(73) Assignee: SUZHOU STAINWEI BIOTECH INC., Jiangsu (CN)

( * ) Notice: Subject to any disclaimer, the term of this patent is extended or adjusted under 35 U.S.C. 154(b) by 0 days.

(21) Appl. No.: 14/651,785

(22) PCT Filed: Nov. 5, 2013

(86) PCT No.: PCT/CN2013/086542
§ 371 (c)(1),
(2) Date: Jun. 12, 2015

(87) PCT Pub. No.: WO2014/090053
PCT Pub. Date: Jun. 19, 2014

(65) Prior Publication Data
US 2016/0039921 A1    Feb. 11, 2016

(30) Foreign Application Priority Data
Dec. 14, 2012  (CN) .......................... 2012 1 0543652

(51) Int. Cl.
*C07K 16/22* (2006.01)
*C07H 21/04* (2006.01)
*A61K 39/395* (2006.01)
*A61P 35/00* (2006.01)
*C12N 15/09* (2006.01)
*C12N 15/63* (2006.01)
*C07K 14/515* (2006.01)
*A61K 39/00* (2006.01)

(52) U.S. Cl.
CPC ........ *C07K 16/22* (2013.01); *A61K 2039/505* (2013.01); *C07K 2317/14* (2013.01); *C07K 2317/20* (2013.01); *C07K 2317/24* (2013.01); *C07K 2317/73* (2013.01); *C07K 2317/76* (2013.01)

(58) Field of Classification Search
None
See application file for complete search history.

(56) References Cited

PUBLICATIONS

Prager et al, 2012. "Angiogenesis in Cancer". Hämostaseologie. 32: 105-114.*

\* cited by examiner

*Primary Examiner* — Zachary Howard
(74) *Attorney, Agent, or Firm* — MKG, LLC

(57) ABSTRACT

A mouse monoclonal antibody for antagonizing and inhibiting binding of a vascular endothelial growth factor (VEGF) and its receptor (VEGF-R), and a heavy chain variable region and light chain variable region amino acid sequence thereof. Also disclosed are a humanized preparation process of the antibody and a heavy chain variable region and light chain variable region amino acid sequence of the humanized antibody. The humanized antibody or its derivative can act as an ingredient of a pharmaceutical composition or be prepared into a suitable pharmaceutical preparation, is administered alone or in combination with a chemotherapy drug or other treatment means, and is used in broad-spectrum treatment of various solid tumors such as colon cancer, breast cancer and rhabdomyosarcoma.

14 Claims, 8 Drawing Sheets

Solubility of antibodies

Relative tumor growth volume (MDA-MB-231 tumor model)

Relative tumor volume growth trend of each group (HCT-8)

MONOCLONAL ANTIBODY FOR ANTAGONIZING AND INHIBITING BINDING OF VASCULAR ENDOTHELIAL GROWTH FACTOR TO ITS RECEPTOR, AND CODING SEQUENCE

FIELD OF THE INVENTION

The present invention belongs to the field of biotechnology involving monoclonal antibodies. The present invention pertains to a monoclonal antibody that can antagonistically inhibit the binding of vascular endothelial growth factor (VEGF) to its receptor (VEGF-R) as well as its applications.

BACKGROUND OF THE INVENTION

In biology, angiogenesis refers to a process of generation of new blood vessels by budding or dividing from the existing blood vessels (capillaries, small arteries and veins) in the body. Angiogenesis is beneficial and essential for maintaining many normal physiological processes, such as embryonic development, wound healing, and repair. On the other hand, excessive blood vessel proliferation or angiogenesis is also associated with pathological processes, such as tumor growth, metastasis and inflammation. The key reason for the in vivo proliferation of the blood vessels is due to the ability of endothelial cells to divide and proliferate incisively and to insert to the existing vascular wall. Vascular endothelial growth factor (VEGF) is the most important and most potent angiogenic factor responsible for vascular endothelial cell growth. The importance of VEGF in angiogenesis has been well demonstrated by studies in VEGF knock-out mice: mouse embryos carrying one copy of VEGF gene, while the other one was knocked-out, would die at 11 to 12 days of development due to a decrease and abnormality in vascular angiogenesis (Carmeliet P et. al., Nature 1996, 380:435; Ferrara N et. al., Nature 196, 380: 439).

Overexpression of VEGF has been observed in a variety of malignancies, such as colorectal, stomach, ovarian, breast cancers, hepatocelluar carcinoma and multiple myeloma; the level of VEGF expression is highly correlated with tumor growth, relapse and metastasis (Dvorak H F et. al: J Exp Med 1991; 174:1275-8; Brown L F et. al., Cancer Res 1993; 53:4727-35; Weidner N, Semple J P, Welch W R and Folkman J: N Engl J Med 1991; 324:1-8.4-5). In recent years, accumulating data from a series of animal experiments have shown that blocking angiogenesis by inhibiting the interaction of VEGF and VEGF-R, via gene manipulation or administration of drugs, leads to tumor ischemia and necrosis, which in turn, results in inhibition of tumor growth, metastasis and ultimately, prolongation of overall survival. Therefore, drug development targeting VEGF mediated angiogenesis has become a hot area of research worldwide.

Currently there are two major approaches to the anti-angiogenesis drug development targeting VEGF and VEGF-R pathway.

The first approach involves an inhibitor that antagonizes the tyrosine kinase located in the intracellular domain of the VEGF receptor (VEGF-R). Such antagonistic inhibitors are generally small-molecule chemical drugs, the prototypic drugs include Sutent (Sunitinib), which was developed and made available on the market in 2006 by Pfizer, and Nexavar (Sorafenib), developed and marketed by Bayer (Germany) and Onyx Pharmaceuticals.

The second approach involves large protein molecules, either an antibody or a fusion protein employing the Fc receptor of an antibody, which can directly block the binding of VEGF to its receptor (VEGF-R). One drug developed via this approach is Avastin (Bevacizumab), a humanized anti-VEGF monoclonal antibody drug which was developed and produced by Roche/Genentech and obtained FDA approval in February 2004. Avastin is so far the only anti-VEGF monoclonal antibody available on the global market. Avastin, by highly specific binding to VEGF, prevents VEGF from binding to VEGF-R, and thus blocks angiogenesis and inhibits tumor proliferation (Presta L G et. al., Cancer Res, 1997, 57: 4593; Hurwitz H et. al., N Engl J Med, 2004; 350:2335). Avastin has currently been approved by the FDA to be used for treatment of metastatic colorectal cancer (mCRC), advanced non-squamous non-small cell lung cancer (NSCLC), glioblastoma, metastatic renal cell carcinoma (mRCC), and various other solid tumors. Avastin also received approval from China SFDA in February 2010 for the treatment of colon cancer.

The precursor of Avastin can be traced back to a mouse monoclonal antibody, A4.6.1. The origin of this antibody, the hybridoma cell lines secreting it, and its use are described in the following patents: U.S. Pat. No. 6,582,959 (inventor: Kim, Kyung Jin; patent date: Jun. 24, 2003; patent title: Antibodies to Vascular Endothelial Growth Factor); and U.S. Pat. No. 7,227,004 (Inventor: Kim, Kyung Jin; patent date: Jun. 5, 2007; patent title: Antibodies to Vascular Endothelial Growth Factor). The amino acid sequence of this murine antibody and its humanized version, rhuMab-VEGF (i.e. Avastin) was published (Presta L G et. al., Cancer Res, 1997, 57: 4593). The method of preparation was disclosed in U.S. Pat. No. 6,054,297 (Inventor: Carter; Paul J. and Presta; Leonard G; patent application date: May 9, 1995; patent date: Apr. 25, 2000; patent title: Humanized Antibodies and Methods for Making Them).

However, this antibody still has the following shortcomings:

1) Similar to most other monoclonal antibodies, monoclonal antibody A4.6.1 (or Avastin) can only bind to a part of VEGF region or epitope, but cannot bind to other epitopes or cover other areas of VEGF antigen.

2) Previous animal experiments and recent clinic research have shown that administering A4.6.1 or Avastin alone was not able to neutralize VEGF entirely, or completely inhibiting VEGF mediated angiogenesis in vivo.

Therefore, it is important and necessary to develop new monoclonal antibodies or therapeutic agents which have the ability to bind to VEGF on new binding sites and same time can inhibit the binding of VEGF to VEGF-R.

SUMMARY OF THE INVENTION

A technical problem to be solved by the present invention is to provide an antibody or antibody derivative which can inhibit the binding of VEGF to VEGF-R. The definition of the antibody in this invention includes a humanized antibody or an antibody derivative, such as a Fab fragment of the antibody and a single chain antibody.

Another technical problem to be solved by the present invention is to provide a DNA molecule or gene that encodes the above antibody.

Another technical problem to be solved by the present invention is to provide a pharmaceutical composition that contains the above antibody.

Another technical problem to be solved by the present invention is to provide a method of preparing the above antibody.

In order to solve the above technical problems, the present invention, in one aspect, provides a murine monoclonal antibody that inhibits the binding of VEGF to VEGF-R. The amino acid sequence of the light-chain variable region of this antibody is shown by SEQ ID NO:1, and the amino acid sequence of the heavy-chain variable region is shown by SEQ ID NO:2. The murine monoclonal antibody was derived from the mouse hybridoma cell line PV19-5, which has been deposited at the Common Microorganism Center of China Microbial Culture Preservation Commission since Mar. 12, 2012 (Accession number: CGMCC No. 5889; Accession location: Beijing, P.R. China). In addition, the present invention also provides DNA molecules encoding the above murine monoclonal antibody, the nucleotide sequence of the light-chain variable region is shown by SEQ ID NO:3 and the nucleotide sequence of the heavy-chain variable region is shown by SEQ ID NO:4.

The present invention, in a second aspect, provides a humanized monoclonal antibody derived from the above murine monoclonal antibody. Compared with the murine monoclonal antibody, the humanized monoclonal antibody, as a therapeutic drug, has advantages of a long half life period of up to 20 days and low immunogenicity in the human body, thus suitable for long-term or repeated use. In the present invention, the protein sequence in both the heavy-chain variable region and the light-chain variable region of the above murine monoclonal antibody were all humanized, which includes amino acid substitutions in framework region, at the sites neighboring the antigen-binding region/complementarity-determining region. The amino acid sequence of the light-chain variable region is shown by SEQ ID NO:5 and the amino acid sequence of the heavy-chain variable region is shown by SEQ ID NO:6. In addition, the present invention also provides DNA sequence encoding the variable regions of this humanized monoclonal antibody, with the nucleotide sequence of the light-chain variable region shown by SEQ ID NO:7 and the nucleotide sequence of the heavy-chain variable region shown by SEQ ID NO:8.

The present invention, in a third aspect, provides a derivative of the above humanized monoclonal antibody, with the amino acid sequence of the light-chain antigen complementarity-determining region (CDR-L) shown by SEQ ID NO:9, SEQ ID NO:10, and SEQ ID NO:11, and the amino acid sequence of the heavy-chain antigen complementarity-determining region (CDR-H) shown by SEQ ID NO:12, SEQ ID NO:13, and SEQ ID NO:14.

The present invention, in a fourth aspect, provides an expression vector, which contains DNA sequence encoding the above humanized monoclonal antibody and an operation sequence necessary for the expression of the above gene.

The present invention, in a fifth aspect, provides a host cell line which has been transfected with the above recombinant expression vector. Both this recombinant host cell line and it offspring cells express the above humanized monoclonal antibody.

The term "monoclonal antibody (mAb)" used herein refers to an immunoglobulin obtained from a clonal cell, which has the same structure and chemical characteristics and is specific for a single antigenic determinant. The monoclonal antibody is different from a conventional polyclonal antibody preparation (typically having different antibodies directed against different determinants), with each monoclonal antibody directed against the same determinant on the antigen. In addition to its specificity, the monoclonal antibody is also advantageous in that it is cultured from hybridomas or recombinant engineering cells, and will not be mixed with other immunoglobulins. The modifier "monoclonal" indicates that the properties of the antibody are achieved from a homogeneous population of antibodies, which should not be interpreted as that any particular method needs to be used for the production of antibodies.

The term "humanized monoclonal antibody" used herein refers to that the amino acid sequences of the human immunoglobulins are substituted for all or most of the amino acid sequences of the murine monoclonal antibodies (including the framework region sequence in the variable region), except the complementarity—determining region (CDR), so as to minimize the immunogenicity of the murine monoclonal antibody.

The terms "antibody" and "immunoglobulin" used herein refer to an isotetraproteoglycan of about 150,000 Daltons having the same structural characteristics, which is composed of two identical light chains (L) and two identical heavy chains (H). Each of the light chains is linked to the heavy chain through a covalent disulfide bond, with the isotype heavy chains of the different immunoglobulins having different amount of disulfide bonds. Each of the heavy and light chains also has regularly spaced intrachain disulfide bonds. Each of the heavy chains is provided at one end with a variable region (VH), following which are a number of invariable regions. Each of the light chains is provided at one end with a variable region (VL), and at the other end with an invariable region; the invariable region of the light chain is opposite to the first invariable region of the heavy chain, and the variable region of the light chain is opposite to the variable region of the heavy chain. Special amino acid residues form an interface between the variable regions of the light chain and heavy chain.

The term "variable" used herein indicates that some portions of the variable region in an antibody are different in sequence, which results in binding of various specific antibodies to the particular antigens thereof as well as the specificity. However, the variability is not evenly distributed throughout the antibody variable region, but concentrated in three segments in the complementarity—determining region (CDR) or hypervariable region in the light-chain and heavy-chain variable regions. The more conservative part in the variable region is called the framework region (FR). The heavy-chain and light-chain variable regions of the antibody each include four FR regions, which are substantially in a β-collapsed configuration and connected by three CDRs forming the connecting loop, with a partially β-collapsed structure possible to be formed in some cases. The CDRs in each chain are close to each other through the FR region and form the antigen-binding site of the antibody together with the CDR of another chain (see Kabat et. al., NIH Publ. No. 91-3242, Vol. 1, pp. 647-669 (1991)). The antibody invariable region does not participate in binding of the antibody to the antigen directly, but it exhibits different effects and functions, such as participating in the antibody-dependent cytotoxicity (ADCC) or complement mediated cytotoxicity (CDC) of the antibody.

The antibody of the present invention can be usually prepared by the following method.

Firstly, insert the gene encoding the antibody of the present invention into the expression vector containing the suitable expression regulatory sequence.

The term "expression regulatory sequence" used herein usually refers to a sequence that participates in control of the gene expression. The expression regulatory sequence includes a promoter operable linked to the target gene as well as a termination signal. The gene (DNA) sequence of the antibody of the present invention can be encoded by the conventional means well known by those skilled in the art, such as artificial synthesis according to the protein sequence disblocked by the present invention or the PCR amplification. Thereafter, the DNA fragment obtained by the synthesis or PCR amplification can be inserted into a suitable expression vector by various methods well known in the art. The expression vector used in the present invention can be an expression vector available on the market that is known for those skilled in the art, such as the pCDNA3.1 expression vector of Invitrogen.

The suitable host cells for accepting the expression vector transformation generally include both prokaryotes and eukaryotes. Examples of commonly used prokaryotic host cells include *E. coli, Bacillus subtilis*. Commonly used eukaryotic host cells include yeast, insect, and mammalian. In the present invention, the preferred host cells are mammalian cells, particularly Chinese hamster ovary (CHO) cells.

The host cells transfected by the expressing vector are cultured under suitable conditions (e.g., the host cells are cultured with a serum-free medium in a cell culture flask or bioreactor by adhesion to the wall or suspension), the supernatant is collected and then purified by conventional separation steps, including protein-A affinity chromatography, ion exchange chromatography, filtration to produce the antibodies of the present invention.

The antibodies of the present invention obtained by purification can be dissolved in an appropriate solvent such as PBS with the desired final concentration allowed to be between 0.1 mg/ml and 100 mg/ml.

The present invention, in a sixth aspect, provides a pharmaceutical composition, which contains a pharmaceutically effective amount of the humanized monoclonal antibody or the derivative thereof as described in the present invention and the pharmaceutically acceptable vector.

The term "pharmaceutically acceptable" used herein refers to that when this antibody and composition are appropriately administered to an animal or human, they will not produce an allergic or other adverse reaction. The "pharmaceutically acceptable vector" used herein should be compatible with the antibody protein of the present invention, i.e. being able to get mixed with it without significantly reducing the effect of the pharmaceutical composition. Specific examples of some substances that can be used as the pharmaceutically acceptable vector or the ingredient thereof include the following substances: sugars, such as lactose, glucose and sucrose; starches, such as corn starch and potato starch; vegetable oils, such as peanut oil, cottonseed oil, sesame oil, olive oil, corn oil and cacao oil; polyhydric alcohols, such as propylene glycol, glycerine, sorbitol, mannitol and polyethylene glycol; alginic acid; emulsifiers, such as Tween; stabilizers; antioxidants; pyrogen-free sterile water for injection; saline solution; phosphate buffer.

The pharmaceutical composition of the present invention can be made into various forms as required, such as lyophilized powder, injection, eye drops and other medication, with the physician determining the dose beneficial to the patient according to the type, age, weight and general disease condition, administration manner, and other factors of patient.

The present invention, in a seventh aspect, provides the application of the above pharmaceutical composition in preparation of a pharmaceutical formulation used for treatment of diseases associated with angiogenesis. In the specific examples of the present invention, the application of the humanized antibody in vivo in inhibition of growth of multiple transplanted tumors such as human colon cancer, breast cancer and rhabdomyosarcoma is described.

The present invention, in an eighth aspect, provides a method of preparing the above humanized monoclonal antibody, which includes the following steps:

a) Providing an expression vector, which contains a DNA sequence encoding the above humanized monoclonal antibody and an expression regulatory sequence linked to this sequence;

b) transforming the host cell with the expression vector of Step a);

c) culturing the host cell from Step b) under conditions suitable for expression of the humanized monoclonal antibody; and d) separating, purifying and collecting the humanized monoclonal antibody from the host cell culture supernatants In order to obtain the monoclonal antibody inhibiting the binding of the human VEGF protein to the receptor thereof (VEGF-R) as well as the hybridoma cell line secreting this antibody, the present invention chose to use recombinant human VEGF165 protein expressed by yeast as antigen and immunized mice by repeated small dose subcutaneous injections until high titers of polyclonal anti-VEGF antibody production was achieved. Spleen cells from selected mice were then obtained and fused with a mouse myeloma cell line. A number of hybridoma cell lines with positive secretion of anti-human VEGF antibodies were obtained. One hybridoma clone, coded PV19, was found to secret antibody capable of specifically recognizing and of a high-affinity binding to human VEGF (including VEGF121, 165, VEGF189 and etc) when tested by ELISA, Western blot, immunohistochemistry and other methods.

In vitro experiments demonstrated that this murine monoclonal antibody effectively inhibited the binding of VEGF to VEGF-R. In the in-vivo xenograft model where human tumor cell lines were transplanted to nude mouse, this murine monoclonal antibody demonstrated inhibition of tumor growth of breast cancer, rhabdomyosarcoma and many others.

The present invention provides the gene encoding the variable regions of the heavy-chain and light-chain after protein separation, purification, genetic engineering and other means. Furthermore, the present invention completed humanization of this antibody on the above basis. The DNA fragment encoding the humanized antibody, was inserted into the expression vector (pCDNA3.1), and transferred to Chinese hamster ovary (CHO) cells to obtain recombinant host cell lines. Pure humanized PV19 antibody, with the biological activity of inhibiting tumor growth in vivo, was obtained from cell culture medium by purification. This humanized antibody can be used as a pharmaceutical component, or prepared into a suitable pharmaceutical formulation, used alone or in combination with chemotherapy drugs and other therapies, for treatment in a broad-spectrum of various solid tumors, such as colon cancer, breast cancer and rhabdomyosarcoma.

The present invention also discloses the humanization process of this antibody, as well as the amino acid sequence of the heavy-chain variable region and light-chain variable region of this humanized antibody.

BRIEF DESCRIPTION OF THE DRAWINGS

FIGS. 8A and 8B are schematic diagrams of experimental results (Example 10 of the present invention), which show that humanized hPV19 antibody inhibits the growth of human Ls-174-T colon cancer in nude mice. Wherein: FIG. 8A shows a relative tumor volume growth trend; and FIG. 8B shows the average tumor weight decrease rate of the respective treatment groups (tumor weight inhibition rate %) compared with the negative control group at the end of the experiment.

FIGS. 9A and 9B are schematic diagrams of experimental results (Example 11 of the present invention), which show that humanized hPV19 antibody inhibits growth of human MD231-MB A breast cancer in nude mice. Wherein: FIG. 9A shows a relative tumor volume growth trend of respective groups during the experiment; and FIG. 9B shows the average tumor weight decrease rate of the respective treatment groups (tumor weight inhibition rate %) compared with the negative control group at the end of the experiment.

FIGS. 10A and 10B are schematic diagrams of experimental results (Example 12 of the present invention), which show that humanized hPV19 antibody inhibits the growth of human A673 rhabdomyoma in nude mice. Wherein: FIG. 10A shows a relative tumor volume growth trend of respective groups during the experiment; and FIG. 10B shows the average tumor weight decrease rate of the respective treatment groups (tumor weight inhibition rate %) compared with the negative control group at the end of the experiment.

FIGS. 11A and 11B are schematic diagrams of experimental results (Example 13 of the present invention), which show that humanized hPV19 antibody inhibits the growth of human HCT8 colon cancer in nude mice. Wherein: FIG. 11A shows a relative tumor volume growth trend of respective groups during the experiment; and FIG. 11B shows the average tumor weight decrease rate of the respective treatment groups (tumor weight inhibition rate %) compared with the negative control group at the end of the experiment.

Figure 1:
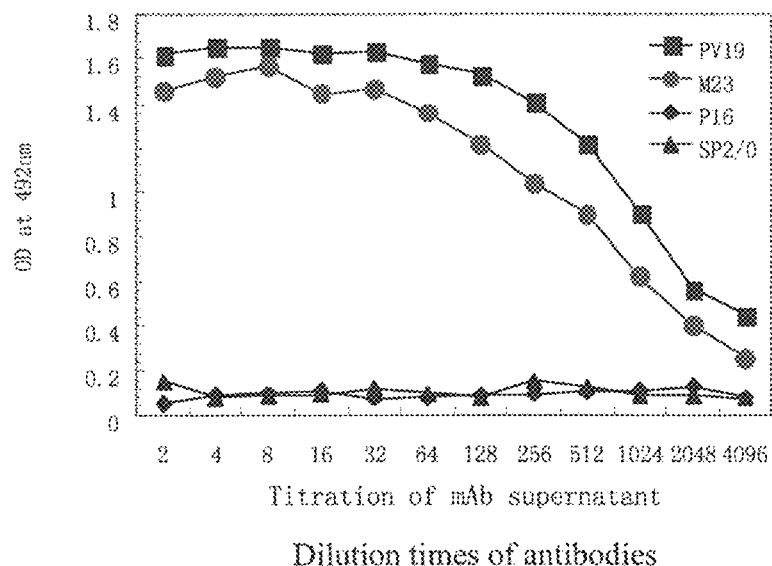
FIG. 1 shows supernatants from mouse hybridoma cell line PV19 binding to human VEGF165 protein coated on the plates (Example 1), Wherein: M23 is supernatant from a hybridoma cell line known to secret anti-human VEGF monoclonal antibody and serves as a positive control; P16, supernatant from an unrelated hybridoma cell line and serves as a negative control; and SP2/0 represents supernatant from an unfused myeloma cell line.

The mouse hybridoma cell line coded PV19-5 has been preserved in Common Microorganism Center of China Microbial Culture Preservation Commission since Mar. 12, 2012 (Accession number: CGMCC No. 5889; Accession location: Institute of Microbiology, Chinese Academy of Sciences, No. 3, Court No. 1, Beichen West Road, Chaoyang District, Beijing, P.R. China).

DETAILED DESCRIPTION OF THE INVENTION

The following examples are offered by way of illustration only and are not intended to limit the invention in any manner.

Example 1

Production and Identification of Mouse Hybridoma Cell Lines Secreting Anti-Vascular Endothelial Growth Factor Antibody

Step 1

Production of Recombinant Human VEGF165 Protein (Immunogen Preparation)

DNA fragments encoding human VEGF165 protein was obtained by PCR using human lung tissue cell cDNA as the template. After being verified by sequencing, a segment was cut out by restriction endonuclease digestion and cloned into pPic9K, a yeast expression vector (Invitrogen Corporation), thus yielding recombinant expression plasmid pPic9K-VEGF165. This plasmid was then introduced into yeast cell *Pichia pastoris*. After fermentation and inducible expression, followed by protein separation and purification, recombinant human VEGF165 protein with greater than 95% purity was obtained.

Step 2

Immunization in Mice a. Balb/c mice were immunized with human VEGF165 protein (100 µl/mouse, 10 µg VEGF165 protein in total) mixed with the Freund's complete adjuvant by multi-point subcutaneous injections. Two to three weeks after the first immunization, the mice were immunized by multi-point subcutanesous injections, with VEGF protein mixed with Freund's incomplete adjuvant. After 2-3 times of boost immunizations, a small amount of serum was collected from each immunized mouse and the titer of anti-VEGF antibody was determined by direct ELISA using VEGF165 protein-coated 96-well plates. Mice with relatively high titers of anti-VEGF antibody were selected and spleens were removed for preparation of cell fusion.

Step 3

Cell Fusion

Three days after the last immunization, mouse spleen was removed and splenocytes were prepared in sterile condition and fused with the mouse Sp2/0 myeloma cells (Purchased from Shanghai Institutes for Biological Sciences, Chinese Academy of Sciences) at a ratio of 5:1 with 50% PEG-1000 (Sigma). The cell fusion was performed following a conventional method (Kohler G. and Milstein C: Nature 1975; 256:495-497). Fused cells were then resuspended at $1 \times 10^6$/ml with RPMI 1640-10% FCS medium containing HAT (Sigma) (wherein H represents hypoxanthine, A represents aminopterin, and T represents thymidine), added into 96-well plates (200 μl/well), and cultured in a 5% $CO_2$ incubator at 37° C. for 2-3 weeks.

Step 4

Screening of Antibody Producing Hybridoma Clones by ELISA

The ELISA microtiter plates were prepared by coating with recombinant human VEGF165 protein (2 μg/ml, pH 9.6, 0.1 M NaHCO3 solution) at 37° C. for 2 hours or overnight at 4° C.; followed by incubation with blocking solution of 2% bovine serum albumin (BSA) overnight at 4° C. After washing with the PBS-0.1% Tween20 (PBST) solution, supernatants from hybridoma cells were added and incubated at 37° C. for 2 hours (unfused Sp2/0 myeloma culture supernatant as a negative control). After washing with the PBS-0.1% Tween20 solution, horseradish peroxidase (HRP)-labeled goat anti-mouse IgG (Sigma) was added and allowed to incubate at 37° C. for 1 hour; after washing completely with the PBS-0.1% Tween20 solution again, substrate solution o-phenylenediamine (OPD)-0.1% $H_2O_2$ was added and allowed to sit for 10-15 min to develop color, followed by addition of a terminating solution of 0.1M HCl. The plates were applied to MK3-Multiskan microplate reader (Thermo Scientific) and OD reading was set at 492 nm. Hybridoma cell lines with a value from OD reading at 492 nm 5-10 times higher than the negative control were subjected to further sub-cloning, expansion and frozen preservation.

Step 5

Subcloning: Limited Dilution of the Positive Hybridoma Cells

The above screened positive cells were diluted to 1-10 cells/well with RPMI-1640-10% FCS medium, added into a 96-well cell culture plate, and cultured in a 5% $CO_2$ incubator at 37° C. for 2-3 weeks.

After cells grown up, supernatants were collected and tested for the presence of anti-VEGF antibody by ELISA again. A number of positive cell lines were identified. After further sub-cloning, a hybridoma cell line coded P19-5 (hereafter referred to as PV19), was found to be able of stable producing anti-VEGF antibody. FIG. 1 shows high titer of anti-VEGF antibody detected in the supernatant from PV19 hybridoma cell line. The antibody produced by PV19 hybridoma was identified to be of IgG. This hybridoma cell line was again amplified and has been passed through multiple generations for a long period of time. The antibody produced by PV19 hybridoma was identified to be of IgG. This hybridoma cell line was also deposited for preservation to the Common Microorganism Center of China Microbial Culture Preservation Commission since Mar. 12, 2012 (Accession number: CGMCC No. 5889; Accession location: Beijing, P.R. China).

Example 2

Production and Purification of Mouse Anti-Human VEGF Monoclonal Antibody (PV19)

Figure 2:
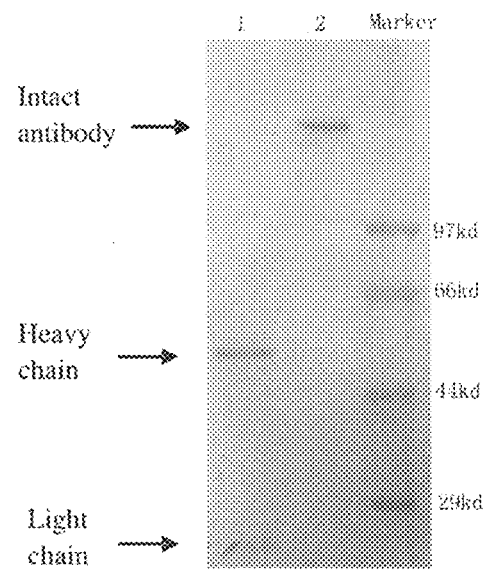
FIG. 2 shows a SDS-PAGE gel analysis of murine PV19 antibody protein. PV19 antibody was purified from PV19 hybridoma cell culture supernatants by affinity chromatography. Lane 1: DTT-reduced PV19 antibody, lane 2: non-reduced PV19 antibody, and Marker: protein molecular weight marker.

Mouse anti-human VEGF monoclonal antibody (PV19) was purified from cell culture supernatants by using an affinity chromatography The purification steps are as follows:

The PV19 hybridoma cells, after being amplified, were inoculated in 200 ml serum-free 1640 medium and cultured at 37° C. for 5 days. Then, the culture supernatants were collected and filtered through a 0.45 μm filtration membrane, before being loaded to an affinity chromatography column containing Protein G-Sepharose Fast Flow (purchased from General Electric). The chromatography column was first subjected to washing with PBS to remove nonspecific proteins; followed by elution of adsorbed PV19 antibody protein with a low pH (2.7-3.0) glycine (0.1M) solution. The elute protein was then adjusted to pH 7.0 with 1 mM Tris (pH 8.5-9.0), dialyzed against PBS (10 times volume of the elute) for 12-16 hours (changing solution 2-3 times). After being filtered through a 0.45 μm filtration membrane, purified PV19 antibody was then obtained The purified PV19 antibody was analyzed by sodium dodecyl sulfate polyacrylamide gel electrophoresis (SDS-PAGE) (10% separating gel, 5% stacking gel) under DTT reducing and non-reducing conditions. FIG. 2 shows the electrophoretic analysis pattern, where lane 1 is DTT-reduced PV19 antibody sample, and lane 2 is non-reduced PV19 antibody sample. As shown in FIG. 2, when compared with non-reduced PV19 antibody sample, DTT-reduced PV19 antibody is separated into two bands, where the upper band represents PV19 antibody heavy chain, and the lower band represents PV19 antibody light chain.

Example 3

Determination of Biological Activity of Murine PV19 Monoclonal Antibody: Inhibition of the Binding of VEGF to VEGF-R by PV19 Monoclonal Antibody One method of determining the biological activity of murine PV19 monoclonal antibody is to use a competitive ELISA to probe the inhibition of the binding of VEGF to VEGF R by PV19 antibody.

The principle and process of this competitive ELISA method are as follows:

First, a fixed amount of biotin-labeled human VEGF165 protein is mixed with serial dilutions of PV19 antibody. The mixtures are then transferred to a 96-well plate pre-coated with soluble VEGF receptor proteins (such as soluble VEGFR1 protein). After incubation and washing, enzyme-labeled Avidin (such as horseradish peroxidase-labeled Avidin) is added into the plate. After another incubation and washing, substrate is added and OD value is measured.

Specifically, the competitive ELISA are as follows:

1) Coat 96-well plate with soluble human VEGFR1 protein (R&D System Inc.) (2 μg/ml, 50 μl/well) at 4° C. overnight;

2) Rinse the plate with PBS-0.1% tween-20 solution (PBS-T) and then block it with 2% BSA (diluted in PBS-T solution) at room temperature for 2 hours; After that, a mixture of a fixed amount of biotin-labeled VEGF165 (Bio-VEGF, 1:1000) with a 2-fold serial dilutions of either PV19 antibody or an unrelated antibody (W10) are added into the plate, and incubate at 37° C. for 2 h;

3) Wash the plate with PBS-T, then add horseradish peroxidase-labeled Avidin (1:5000), and incubate at 37° C. for 1 h;

4) Wash the plate with PBS-T again, and then add OPD-3% hydrogen peroxide; incubate at room temperature for 10 min or until the color is developed;

5) Stop the reaction by adding 0.1 M HCL and measure the absorbance of each well at a wavelength of 492 nm.

Figure 3:
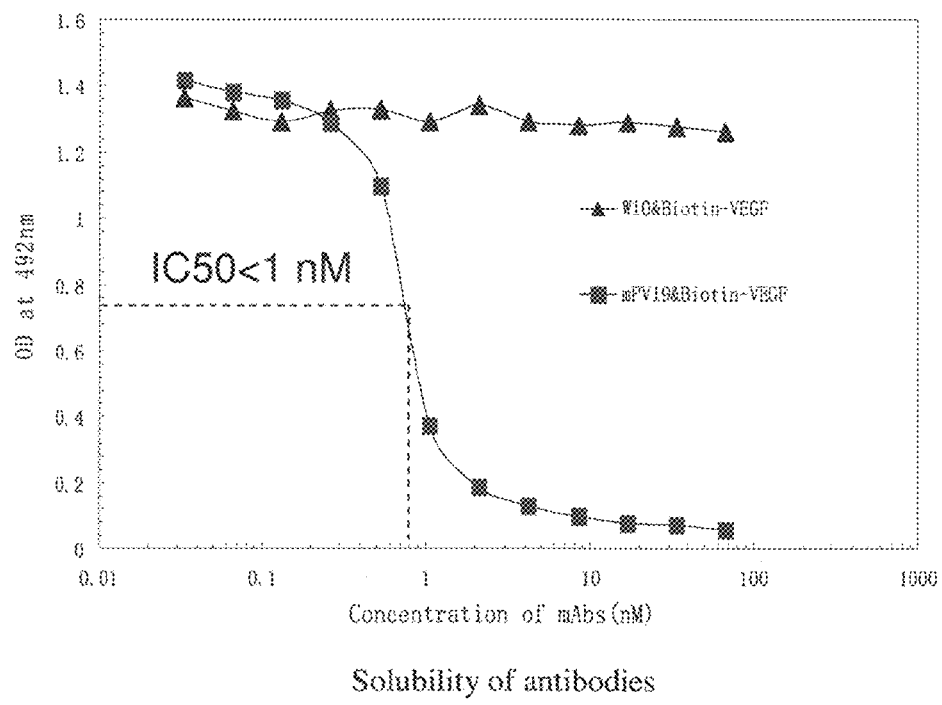
FIG. 3 is a representative schematic diagram showing a competitive ELISA result (in Example 3), wherein mPV19 & Biotin-VEGF is a mixture of PV19 antibody and biotin-VEGF, and W10 & Biotin-VEGF is a mixture of an unrelated antibody W10 and biotin-VEGF (serves as a negative control).

FIG. 3 shows a representative result of this competitive ELISA. As shown in FIG. 3, in PV19 antibody (mPV19 & Biotin-VEGF) group, the OD value is inversely correlated with the amount of the antibody protein; i.e., the more the amount of the PV19 antibody is, the lower its OD value will be, whereas in unrelated antibody (W10 & Biotin-VEGF) group, the OD value is not affected by the dilutions of W10 antibody. These results demonstrate that PV19 antibody is able to block the binding of VEGF to its receptor (VEGFR1).

Example 4

Clone the Gene Encoding the Murine PV19 Antibody Variable Region

Purified PV19 antibody was separated into two bands corresponding of the heavy and the light chain, respectively by SDS-PAGE under DTT reducing condition and then transferred to a PVDF membrane. The membrane was stained with coomassie brilliant blue R250 and the two bands of PV19 antibody heavy and light chain were cut and subject to N-terminal amino acid sequencing by Edman degradation method. The N-terminal amino acid sequence of the light chain was successfully obtained. However, due to N-terminal end blocking, the N-terminal amino acid sequence of the heavy chain cannot be determined.

Procedure for Cloning PV19 Antibody Light Chain Variable Region DNA

Step 1. Extract total RNA from the mouse PV19 hybridoma cell with a kit (Jiangsu Haimen Biyuntian Co.).

Step 2. Use reverse transcription PCR (RT-PCR) method (reaction done in an eppendorf tube), to obtain the cDNA template by using the primer (mIg-kappa):

```
                                        (SEQ ID NO: 15)
        TGTCGTTCACTGCCATCAAT;
```

RT-PCR Reaction System:

| Primer | 2 µl |
| Total RNA | 30 µl |

Incubate at 72° C. for 10 minutes, and then keep on ice for 2 minutes.

After that, Add the Following Reagents:

| 5X RT-PCR reaction buffer | 10 µl |
| dNTPs | 5 µl |
| PrimeScript reverse transcriptase | 1.5 µl |

-continued

| Distilled water | 1.5 µl |
| Total volume | 50 µl |

RT-PCR Reaction was carried out at 42° C. for 1 hour, after that raised the temperature to 75° C. and hold for 15 minutes to inactivate the reaction. The obtained cDNA was then stored at −20° C.

Step 3. Design the following primers according to the N-terminal amino acid sequence of PV19 antibody light chain:

```
Forward primer (5' primer):
                                        (SEQ ID NO: 16)
GAC ATT GTG ATG TCA CAG TCT CCA T Reverse primer (3' primer):
                                        (SEQ ID NO: 17)
AAT TGG ATC CAG TTG GTG CAG CAT CAG C
```

Use the above primers and the cDNA obtained in Step 2 as the template to set up a PCR amplification, wherein the PCR amplification of the light chain DNA is as follows:

| Forward primer | 5 µl |
| Reverse primer | 5 µl |
| 2.5 mmol/L dNTPs | 5 µl |
| 10X Reaction buffer | 5 µl |
| cDNA template | 2 µl |
| pfu DNA polymerase | 0.5 µl |
| Distilled water | 27.5 µl |
| Total volume | 50 µl |

The PCR reaction cycle parameters are as follows:

| 94° C. 5 m | |
| 94° C. 30 s | 30 cycles |
| 56° C. 30 s | |
| 72° C. 1 m | |
| 72° C. 10 m | |

Step 4. Separate the PCR reaction products in a 1% agarose gel by electrophoresis. After electrophoresis, cutting off the separated DNA band, and sequencing it, thus obtaining the nucleotide sequence of PV19 antibody light chain variable region DNA.

The nucleotide sequence of PV19 antibody light chain variable region is shown by SEQ ID NO:3, and the deduced amino acid sequence is shown by SEQ ID NO:1, The amino acid sequences of the CDR1, CDR2 and CDR3 of this light chain are shown by SEQ ID NO:9, SEQ ID NO:10 and SEQ ID NO:11, respectively.

Procedure for Cloning PV19 Antibody Heavy Chain Variable Region DNA

Due to a lack of N-terminal amino acid sequence information, a degenerate primer PCR method is used for cloning the gene encoding PV19 antibody heavy chain variable region.

The primers used for this PCR amplification are as the follows:

```
Forward primer (5' primer):
TCA G GCC ATT ACG GCC MMY CWM ACC AT
(as shown by SEQ ID NO: 18), wherein M represents
A or C, Y represents C or T, W represents A or T.

Reverse primer (3' primer):
AAT TGG ATC CTG GGG GTG TCG TTT TGG C
(as shown by SEQ ID NO: 19).
```

By using the above primers and cDNA prepared from the mouse PV19 hybridoma cell line as the template, a PCR reaction (PCR reaction system and parameters were similar to the above light chain PCR reaction) resulted in an amplification of a DNA fragment corresponding to the PV19 antibody heavy chain variable region. The PCR-amplified DNA was electrophoretically analyzed in a 1% agarose gel. After electrophoresis, DNA band was cut and subject to sequencing. The nucleotide sequence of PV19 antibody heavy chain variable region is shown by SEQ ID NO:4, and the deduced amino acid is shown by SEQ ID NO:2. The amino acid sequences of CDR1, CDR2 and CDR3 of this heavy chain are shown by SEQ ID NO:12, SEQ ID NO:13 and SEQ ID NO:14, respectively.

Example 5

Generation of Mouse-Human Chimeric PV19 Antibody (chPV19)

By fusing the DNA fragment of PV19 antibody light chain variable region (described in Example 4) with a DNA fragment of human-kappa light chain invariable region (C-domain), a mouse-human chimeric PV19 antibody light chain (chPV19-L) was obtained. By fusing the DNA fragment of PV19 antibody heavy chain variable region (described in Example 4) with a DNA fragment of human IgG1-heavy chain invariable region (C-domain), a mouse-human chimeric PV19 antibody heavy chain (chPV19-H) was also obtained. Both the chimeric PV19 antibody light chain (chPV19-L) and heavy chain (chPV19-H) were inserted into the pcDNA3.1 expression plasmid, and the expression plasmid was then introduced into E. coli for plasmid DNA amplification. Large amount of expression plasmid were obtained.

The expression plasmids containing the mouse-human chimeric PV19 antibody gene were then mixed with liposomes (Fugen6, from Roche) and transfected into the Chinese hamster ovary (CHO) cells. Two to three days after transfection, cell culture supernatants were collected and the VEGF-binding activity was determined by ELISA. The ELISA was done in 96-well plates pre-coated with human VEGF165 protein, with HRP-labeled goat-anti-human-IgG as the secondary antibody (detection antibody) (purchased from Shanghai Xitang Biotechnology Co.). ELISA results demonstrated that chimeric antibody (chPV19) present in the supernatants from CHO cells transfected with this plasmid DNA was able to bind to human VEGF protein.

Example 6

Initial Engineering Verification of the Humanized PV19 Antibody (hPV19)

After demonstrating high affinity binding of the mouse-human chimeric antibody (chPV19) to human VEGF protein by ELISA, a humanized version of PV19 was engineered as follows. The antigen complementarity-determining regions (CDRs) of mouse PV19 antibody light chain and PV19 antibody heavy chain were identified and transplanted into the corresponding human kappa-light chain framework region and human IgG1-heavy chain variable framework region, respectively, thus generated a humanized version of PV19 antibody.

Humanization of the Light Chain of PV19 Antibody

By amino acid sequence analysis, it was found that the germline gene encoding the fourth V region of the human immunoglobulin kappa light chain (IgkV4-1, Gene ID: 28908) has the highest homology with the light chain sequence of PV19. Therefore, as a first step, the coding sequence of the variable region of PV19 light chain was linked to the human immunoglobulin kappa light chain invariable region (GenBank: BC095489.1), thus yielding a full-length chimeric light chain gene (cPV19-L). In the next step, the cPV19-L light chain framework region (FR) was substituted by the homologous sequence of the human IgkV4-1 by recombinant DNA technique, successfully yielding a humanized PV19 light chain coding sequence (hPV19-L). The amino acid sequence of this humanized hPV19 antibody light chain variable region is shown by SEQ ID NO:5.

Humanization of the Heavy Chain

By amino acid sequence analysis, it was found that the seventh V region germline gene of the human immunoglobulin heavy chain (IgHV7-81, NCBI Gene: 28378) has the highest homology with the heavy chain sequence of PV19. Therefore, as a first step, the coding sequence of the variable region of the PV19 antibody heavy chain was linked to the human immunoglobulin IgG-Gamma1 chain invariable region (GenBank: BC073782.1), yielding a full length chimeric heavy chain gene (cPV19-H). In the next step, the cPV19-H framework region (FR) was substituted by the homologous sequence of the human IgHV7-81 by recombinant DNA technique, successfully yielding a humanized PV19 heavy chain coding sequence (hPV19-H). The amino acid sequence of this humanized hPV19 antibody heavy chain variable region is shown by SEQ ID NO:6.

The DNA fragments encoding the chimeric heavy chain (cPV19H), the chimeric light chain (cPV19L), the humanized heavy chain (hPV19H), and the humanized light chain (hPV19L) were individually inserted into the pcDNA3.1 expression vector, to generate four different recombinant DNA expression plasmids. These plasmid DNA, in a pair-wise combination, were transferred into Chinese hamster ovary cells (CHO) for gene expression. Forty-eight hours after transfection, cell culture supernatants were collected and added into plates pre-coated with VEGF165 protein. The VEGF-binding antibody was then detected by ELISA using HRP-labeled goat-anti-human-IgG antibody (purchased from Shanghai Xitang Biotechnology Co.) as the secondary antibody and o-phenylenediamine (OPD) as the color-developing substrate.

The ELISA result was shown in Table 1. The data showed that like the chimeric version of PV19 antibody, the humanized version of PV19 antibody can also bind to human VEGF165 protein.

TABLE 1

Detection of VEGF-binding antibodies in the supernatants from transiently transfected cells by ELISA

| Supernatant dilution | OD value | | | |
|---|---|---|---|---|
| | cPV19H + cPV19L | cPV19H + hPV19L | hPV19H + cPV19L | hPV19H + hPV19L |
| 2 | 2.933 | 2.904 | 2.688 | 2.632 |
| 4 | 2.762 | 2.718 | 1.976 | 2.291 |
| 8 | 2.451 | 2.438 | 1.33 | 1.745 |
| 16 | 1.745 | 1.769 | 0.888 | 1.207 |
| 32 | 0.967 | 1.14 | 0.591 | 0.874 |
| 64 | 0.762 | 0.776 | 0.408 | 0.598 |
| 128 | 0.632 | 0.585 | 0.337 | 0.476 |
| 256 | 0.524 | 0.465 | 0.312 | 0.517 |

Example 7

Selection and Generation of Engineering Cells that Stable Express hPV19 Antibody In order to obtain engineering cells that stably express and secrete hPV19 antibody to a level suitable for industry application, one approach as shown in this example of the present invention is as follows: first insert the gene containing the humanized HPV19 antibody heavy or light chains simultaneously into a pCDNA3.1-DHFR expression plasmid which containing hamster dihydrofolate reductase (DHFR) genes, thus yield an recombinant plasmid called pQY-hPV19D-DHFR. Then, mix this recombinant expression plasmid DNA with a liposome and transfect into human DHFR-deficient Chinese hamster ovary cells (CHO-DHFR$^{-/-}$). The transfected cells are then cultured in medium containing methotrexate (MTX). By gradually increasing the concentration of MTX in the culture medium, the copy number of DHFR gene (and also antibody gene) in the transfected cells are increased, which in turn, results in an enhanced antibody protein expression. Thus, cell lines that stably and efficiently express humanized hPV19 antibodies are obtained.

The processes for the construction of this recombinant plasmid as well as the screening, MTX selection of these engineering cell lines are as follows:

Construction of an Expression Plasmid (phPV19D-DHFR) Containing hPV19 Antibody Gene and DHFR Gene In this example, a pCDNA3.1 based plasmid (pCDNA3.1-DHFR) which contains hamster dihydrofolate reductase (DHFR) gene was used as the cloning vector. Humanized hPV19 antibody light chain (hPV19L) and heavy chain (hPV19) were simultaneously inserted into this plasmid, thus obtaining an recombiant expression plasmid called pQY-hPV19-DHFR. In this recombinant expression plasmid, the promoter used to drive the expression of DHFR gene in mammalian cells is the SV40 early promoter (pSV40), while the promoter for driving hPV19 antibody light chain gene (hPV19L) expression is the human elongation factor 1-α subunit promoter (pEF1-a), and the promoter for driving hPV19 antibody heavy chain gene (hPV19H) expression is the cytomegalovirus early promoter (pCMV).

Preliminary Screening of Engineering Cell Lines

FUGENE-HD liposomes (from Roche) was used as the transfection reagent to introduce DNA into cells. Briefly, mix the above expression plasmids phPV19D-DHFR with FUGENE-HD liposomes, and then add into DHFR deficient Chinese hamster ovary cells (CHO-DHFR$^-$). Forty-eight hours after the transfection, cell culture medium were removed and transferred into 96-well plates pre-coated with human VEGF165 protein, the VEGF-antibody binding activity was determined by a direct ELISA method as described in Example 6. ELISA assay results showed that cell culture medium from transfected cells contains antibody capable of binding to human VEGF165 antigen.

After being treated with trypsin solution, these transfected cells were removed and resuspended in HT-free IMDM medium, and then added into 96-well cell culture plates by a limiting dilution method. After being cultured for 5-7 days, cell culture medium was screened for the presence of VEGF-binding antibody by ELISA. A total of about 400 individual cell clones were screened and 380 were found to be positive (giving a positive clone ratio of 95%) with the titer of antibody expression between 1-10 μg/ml.

Further Selection and Screening of Cell Lines by Increasing the Concentration of Methotrexate A number of positive cell lines with relatively high-levels of antibody expression were picked up and inoculated into 24-well cell culture plates for further selection by gradually increasing the concentration of MTX presented in the culture medium.

At the first round (initial) round of selection, the MTX concentration was set at 5 nM. After being cultured for 3-4 days, supernatants were collected and the titer of hPV19 antibody was determined by the same ELISA method. Those clones with even higher level of antibody expression were picked up and inoculated into new 24-well cell culture plates and entering into next round (Round 2) selection (MTX concentration of this round increased to 10 nM); this selection and screening process were continued by several more rounds until the MTX concentration in the medium was reached to over 320 nM. After a total of 7-8 rounds of selection/screening, several clones were found to have antibody protein expression titer up to 150-200 μg/ml (compared with the case before the MTX selection, the antibody protein expression level is increased by more than 20 times). Some of these high-expression clones were further adapted to suspension culture in serum-free media. Without medium optimization of culture process, the level of hPV19 antibody produced by these cell lines were found to be in the range between 150-200 μg/ml, which is similar to the expression level before the adaptation.

Example 8

Large-Scale Production and Characterization of Humanized Antibody (hPV19)

Figure 4:
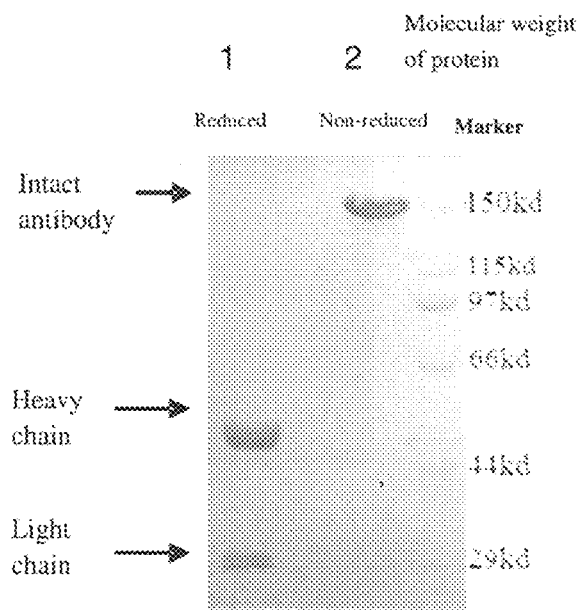
FIG. 4 shows the SDS-PAGE gel analysis of humanized hPV19 antibody protein (in Example 8 of the present invention). hPV19 antibody was obtained from the culture supernatant through purification with an affinity chromatography column. Lane 1: DTT-reduced hPV19 antibody, lane 2: non-reduced hPV19 antibody, and Marker: protein molecular weight marker.

The above cell lines, which have been adopted in suspension culture with serum-free medium, were transferred to culture flasks or bioreactors for further amplification. Supernatants were collected from these cultures and loaded onto protein-A affinity chromatography for antibody purification. After being processed through ion exchange chromatography, viral inactivation and filtration, greater than 99% pure humanized hPV19 antibody were obtained. FIG. 4 is a representative pattern of the SDS-PAGE electrophoresis of purified hPV19 antibody under DTT reducing and non-reducing conditions, wherein lane 1 represents the DTT-reduced antibody, and lane 2 represents the non-reduced antibody. The SDS-PAGE gel results showed that under DTT-reduced condition, hPV19 antibody was separated into two bands, wherein the upper band represents the heavy chain, and the lower band represents the light chain; under non-reduced condition, hPV19 antibody was located near 150 kD area, which is consistent with the theoretically expected molecular weight of a full IgG1 antibody.

Figure 5:
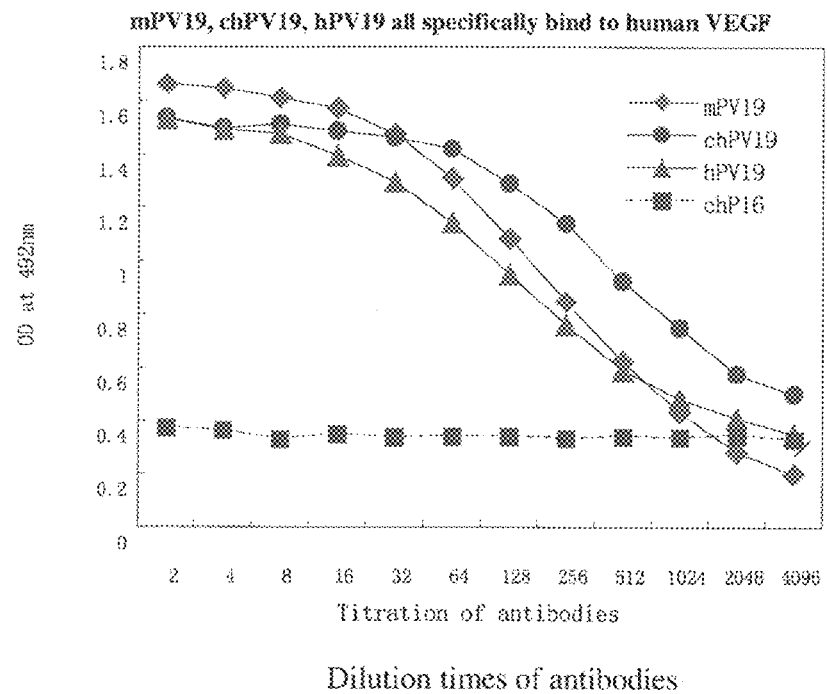
FIG. 5 is a schematic diagram of an experiment result (Example 8 of the present invention), which show the relative binding of humanized antibody (hPV19), chimeric antibody (chPV19), and murine antibody (mPV19) to human VEGF165 protein, as measured by direct ELISA. ChP16, an unrelated chimeric antibody, is a negative control.

The VEGF-binding activity of humanized antibody (hPV19), chimeric antibody (chPV19), and murine antibody (mPV19) was determined by a direct ELISA method as that described in Example 5. FIG. 5 shows a representative ELISA result, which showed that humanized antibody (hPV19) maintains VEGF165-binding activity, with a potency very close to its parental murine antibody (mPV19).

Figure 6:
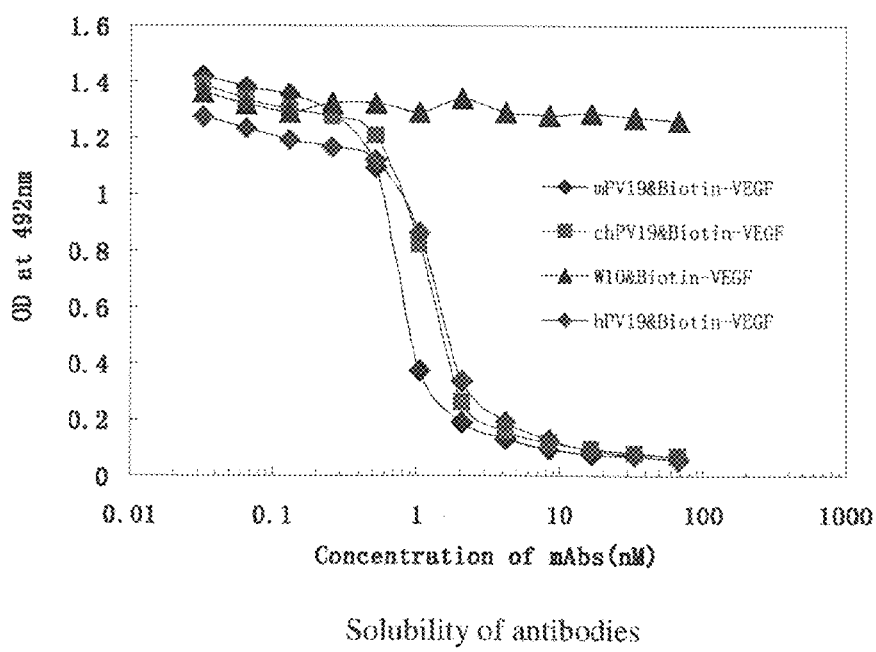
FIG. 6 is a schematic diagram of a competitive ELISA results of Example 8 of the present invention, which shows the in-vitro blocking of the binding of biotin-human VEGF165 protein (bio-VEGF) to VEGFR1 by humanized antibody (hPV19), chimeric antibody (chPV19), and murine antibody (mPV19). W10, an unrelated chimeric antibody, is a negative control.

The blocking of binding of human VEGF165 protein (biotin-VEGF) to its receptor (VEGFR1) by humanized antibody (hPV19), chimeric antibody (chPV19) and murine antibody (mPV19) was determined by a competitive ELISA method as that described in Example 6. FIG. 6 shows a representative result of this competitive ELISA result, which showed that humanized antibody (hPV19) can block the binding of VEGF to VEGFR1, with a potency very close to its parental murine antibody (mPV19).

Example 9

Determination of VEGF-Binding Site by the hPV19 Antibody and Avastin

According to the literature, the key antigenic epitope recognized by A4.6.1 (Avastin) on human VEGF protein is near the glycine at the $88^{th}$ site (Gly, G88); if this glycine is mutated into alanine (G88/A point mutation), the binding of A4.6.1 or Avastin) to this mutant VEGF is significantly decreased.

In order to determine if the VEGF binding site (epitope) recognized by hPV19 antibody has any difference with that of recognized by Avastin, human VEGF165 protein with a G88/A point mutation (Gly change to Ala) was generated. This mutant VEGF, along with the wild-type VEGF, were used as capture antigens to probe the relative binding affinity of hPV19 antibody and of Avastin in ELISA method. Wherein the specific implementation steps and results are described as follows:

Step 1

Expression and Purification of VEGF Protein with G88/A Mutation

Here, an overlap extension PCR method was used for generating VEGF molecule with a point mutation. The overlap extension PCR technology (whole name: gene splicing by overlap extension PCR, referred to as SOE PCR), due to the use of a primer having a complementary end, makes the PCR product form an overlapping chain; thereby by extension of the overlapping chain in the subsequent amplification reaction, overlapping and splicing the amplified fragments of different sources; this technology can be effective in genetic recombination in vitro, and does not require endonuclease digestion and ligase treatment, allowing to quickly obtain products that are difficult to obtain by other restriction endonuclease digestion methods; the key of success of the overlap extension PCR technology is the design of the overlap complementary primers, with the overlap extension PCR having its broad and unique applications in site-directed mutations of genes, construction of fused genes, synthesis of long-segment genes, gene knockout, amplification of the target genes, and other aspects.

By using a pair of the following primers (forward primer: VEGFG88F: CCT CAC CAA GCC CAG CAC ATA, as shown by SEQ ID NO:20; reverse primer: VEGFG88R: CTA TGT GCT GGG CTT GGT GAG, as shown by SEQ ID NO:21), the overlap extension PCR results in the amplification of a cDNA fragment encoding human VEGF165 with G88/A point mutation. This mutant VEGF DNA fragment was then inserted into pPic9K expression vector, and the recombinant plasmid was then introduced into the yeast *Pichia pastoris* GS115 strain cells. The mutant VEGF protein was then expressed and purified.

Steps 2

Determine the Relative Binding Affinity of hPV19 and Avastin to Either Wild-Type and Mutant VEGF165 Protein The general experimental procedures for this section are as the follows:

1) Coat a 96-well ELISA plate with either wild-type human VEGF165 or mutant VEGF protein (VEGF G88/A)

2) A serial of 2-fold dilutions of hPV19 antibody and Avastin are added to the 96-well plate, incubate at 37° C. for 1 hour.

3) Wash the plate with PBST and then add HRP-goat anti-human-Fc antibody (diluted at 1:2000).

4) Wash the plate again, and then add the substrate OPD to develop color.

Figure 7:
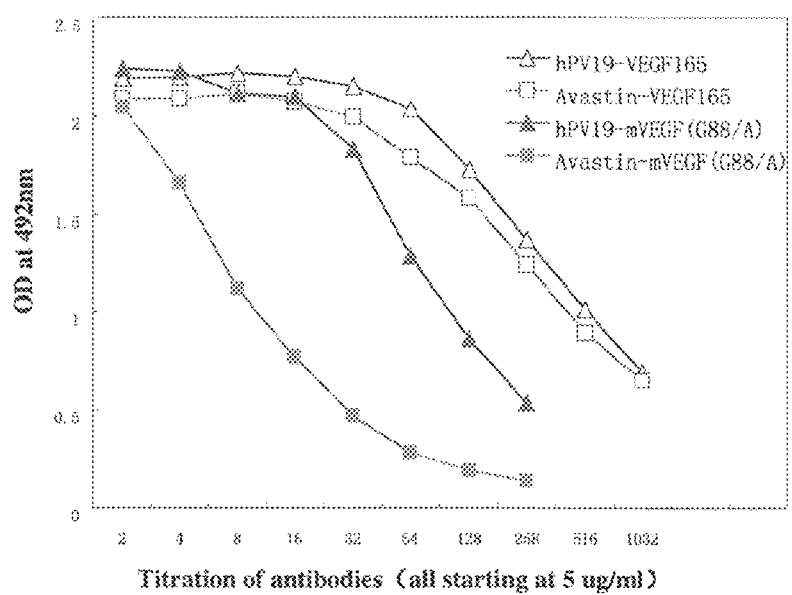
FIG. 7 is a schematic diagram of an experiment result (Example 9 of the present invention), which show the relative binding of humanized hPV19 antibody and Avastin to either wild-type (VEGF165) or mutant VEGF protein (VEGF-G88/A).

The ELISA results are shown in FIG. 7. As shown in FIG. 7, the relative binding of hPV19 antibody and Avastin to the wild-type human VEGF165 are very close to each other; on the other hand, the relative binding of hPV19 antibody and Avastin to the mutant VEGF protein (VEGF G88/A) protein are remarkably different; compared with its binding to the wild-type human VEGF165, the binding of Avastin to the mutant VEGF protein (VEGF G88/A) protein was reduced by about 25 to 50 fold; while the binding of hPV19 to the mutant VEGF protein (VEGF G88/A) protein was only reduced about 3 to 6 fold. These results indicate that the binding site of hPV19 antibody to human VEGF protein is not the same as that of Avastin.

Example 10

Humanized hPV19 Antibody Inhibiting the Growth of Transplanted Human Ls-174-T Colon Cancer Cells in Nude Mice Step 1

Establishment of Human Ls-174-T Colon Cancer Model in Transplanted Nude Mice

Two nude mice were prepared to serve as tumor bearing mice. $1\times10^7$ of human Ls-174-T colon cancer cells (purchased from Cell Preservation Center of Shanghai Institutes for Biological Sciences, Chinese Academy of Sciences) at the log-growth cycle, or tumor mass in a size of about 1.5 mm³, were inoculated subcutaneously into the right armpit of these two nude mice. Once the tumor grows to a size about 400-600 mm³, tumor bearing mice which appeared to be healthy and in good condition were selected and the tumor was removed under aseptic conditions and processed to a form of 1.5 mm³ tumor nodules to be used to inoculate experimental mice, subcutaneously in the right armpits, for treatment experiments.

Nude mice inoculated with tumor nodules were observed for tumor growth. When the tumor volume reached about 50-100 mm³, a screening was done and those mice bearing tumors too small or too large in size were excluded. The selected mice were then randomly divided into different groups for different doses of drugs

Step 2

Treatment of Transplanted Human Ls-174-T Colon Cancer by Humanized PV19 Antibody The above nude mice inoculated with Ls-174-T colon cancer were divided into the following five treatment groups (8 mice/group). Antibodies were injected intraperitoneally twice a week for 4 weeks.

Treatment Groups are as Follows:
1) high-dose humanized hPV19 antibody group (high-dose group, 10 mg/kg body weight);
2) medium-dose humanized hPV19 antibody group (medium-dose group, 5 mg/kg body weight);
3) low-dose humanized hPV19 antibody group (low-dose group, 2.5 mg/kg body weight);
4) Avastin control group (5 mg/kg body weight); and
5) Saline negative control group.

During the treatment, mice were observed for general clinical symptoms twice a day, and the body weight and tumor diameters were measured twice a week. At the end of experiment, tumors were removed after euthanasia, and the tumor weight were measured. The treatment effect was measured by the ratio of tumor size in the testing group (T) versus the control group (C), i.e. T/C %. If T/C %≤40, and p value <0.05, the treatment was considered to be effective, while taking the tumor weight inhibition rate of greater than 60% as the validity reference index.

Treatment Results:
Effect on the Tumor Growth
After the first administration, both the long and short diameters of tumors were recorded twice a week, and tumor volume (V) and the relative tumor volume (RTV) were calculated. The calculation formula for RTV is: RTV=Vt/Vo, where Vt is the tumor volume measured at each time point (day), and Vo is the initial (before administration) tumor volume.

Figure 8A:
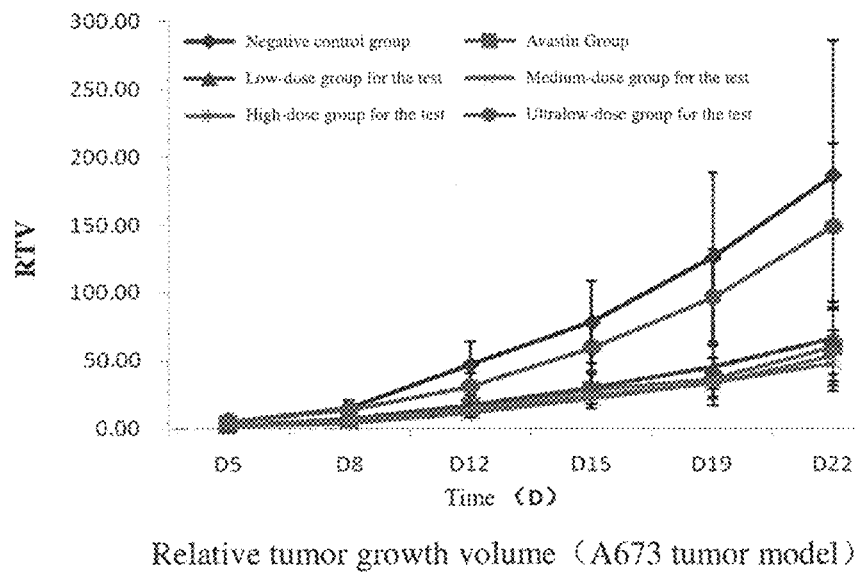

The relative tumor volume growth trend of Ls-174-T tumor in each group was shown in FIG. 8A, compared with the saline negative control group, humanized hPV19 antibody treatment significantly inhibited tumor growth.

Effect on Tumor Weight
At day 29, each animal was euthanized, and its tumor was removed and weighted and the average tumor weight in each group was calculated.

The saline negative control group had an average tumor weight of 2.957 g.

The Avastin group had an average tumor weight of 0.767 g, which is significantly lower than that of the negative control group (P≤0.01).

The average tumor weight of the low, medium and high dose treatment groups using humanized hPV19 antibody were 0.883 g, 0.631 g and 0.467 g, respectively, which were all significantly lower than that the negative control group (P≤0.01 or P≤0.001).

Figure 8B:
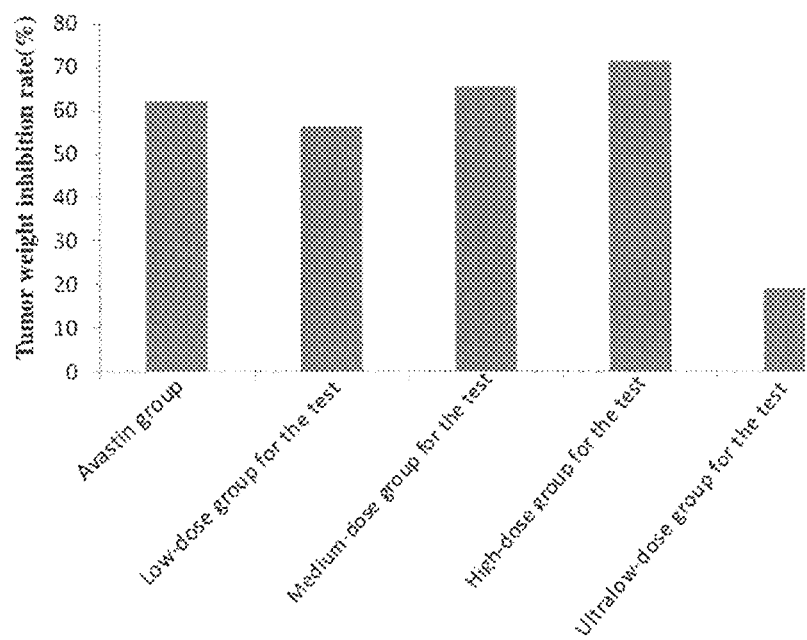

The tumor weight inhibition rate was shown in FIG. 8B. Avastin treatment group had a tumor weight inhibition rate of 74.05%, and the low, medium and high dose of hPV19 antibody treatment groups had tumor weight inhibition rates of 70.15%, 78.66%, 84.21%, respectively. These results demonstrated that hPV19 antibody can significantly inhibit tumor growth, and the degree of inhibition was similar to that of Avastin.

Example 11

Humanized hPV19 Monoclonal Antibody Inhibiting the Growth of Transplanted Human MDA-MB-231 Breast Cancer in Nude Mice

Step 1

Establishment of Transplanted Human MDA-MB-231 Breast Cancer Model in Nude Mouse The tumor model establishment is basically the same as that in Example 10.

Nude mice were inoculated with human MDA-MB-231 breast cancer. When the tumor volume reached about 50-100 $mm^3$, a screening was done and those mice bearing tumors too small or too large in size were excluded. The selected mice were then randomly divided into different groups for different doses of drugs

Step 2

Treatment of Transplanted Human MDA-MB-231 Breast Cancers with Humanized PV19 Antibody The above nude mice inoculated with human MDA-MB-231 breast cancer were divided into the following five treatment groups (7 mice/group). Antibodies were injected intraperitoneally twice a week for 5 weeks, and ending the test on the $36^{th}$ day (D36).

Treatment Groups are as Follows:
1) high-dose humanized hPV19 antibody group (high-dose group, 10 mg/kg body weight);
2) medium-dose humanized hPV19 antibody group (medium-dose group, 5 mg/kg body weight);
3) low-dose humanized hPV19 antibody group (low-dose group, 2.5 mg/kg body weight);
4) Avastin control group (5 mg/kg body weight); and
5) Saline negative control group.

During the treatment, mice were observed for general clinical symptoms twice a day, and the body weight and tumor diameters were measured twice a week. At the end of experiment, tumors were removed after euthanasia, and the tumor weight were measured. The treatment effect was measured by the ratio of tumor size in the testing group (T) versus the control group (C), i.e. T/C %. If T/C %≤40, and p value<0.05, the treatment was considered to be effective, while taking the tumor weight inhibition rate of greater than 60% as the validity reference index.

Figure 9A:
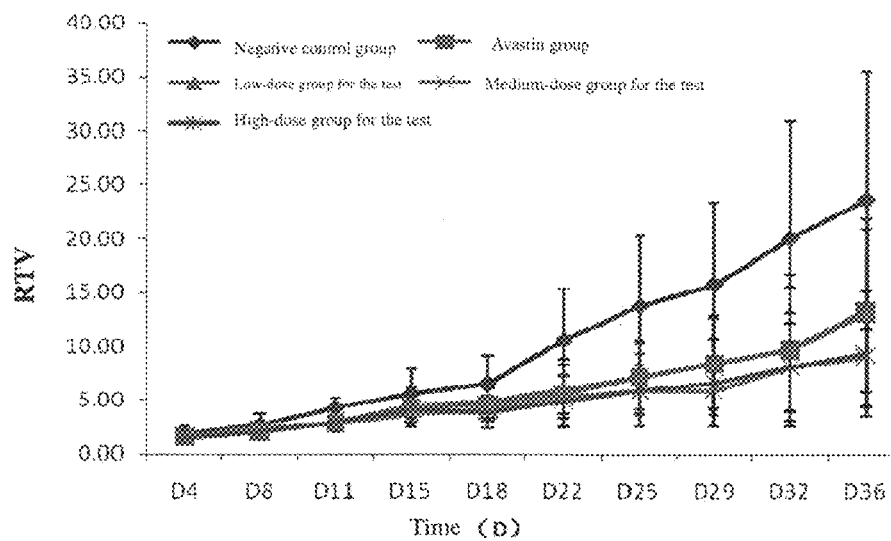

Treatment Results:
Effect on Tumor Growth
After the first administration, the long and short diameters of the tumor were measured twice a week, and the tumor volume (V) and the relative tumor volume RTV thereof (Vt/VO) were calculated. The relative tumor volume growth trend of MDA-MA-231 tumor in each group was shown in FIG. 9A. As shown in the FIG. 9A, compared with saline negative control group, humanized hPV19 antibody can significantly inhibit the tumor growth.

Effect on Tumor Weight

At day 36, each animal was euthanized, and its tumor was removed and weighted and the average tumor weight in each group was calculated.

The negative control group has the average tumor weight of 0.890 g.

The Avastin group has the average tumor weight of 0.543 g, which is not significantly different compared to the negative control group (P>0.05).

The low, medium and high dose groups of the humanized hPV19 antibody have the average tumor weights of 0.576 g, 0.298 g and 0.357 g, respectively, which are not significantly different compared to the negative control group (P>0.05).

Figure 9B:
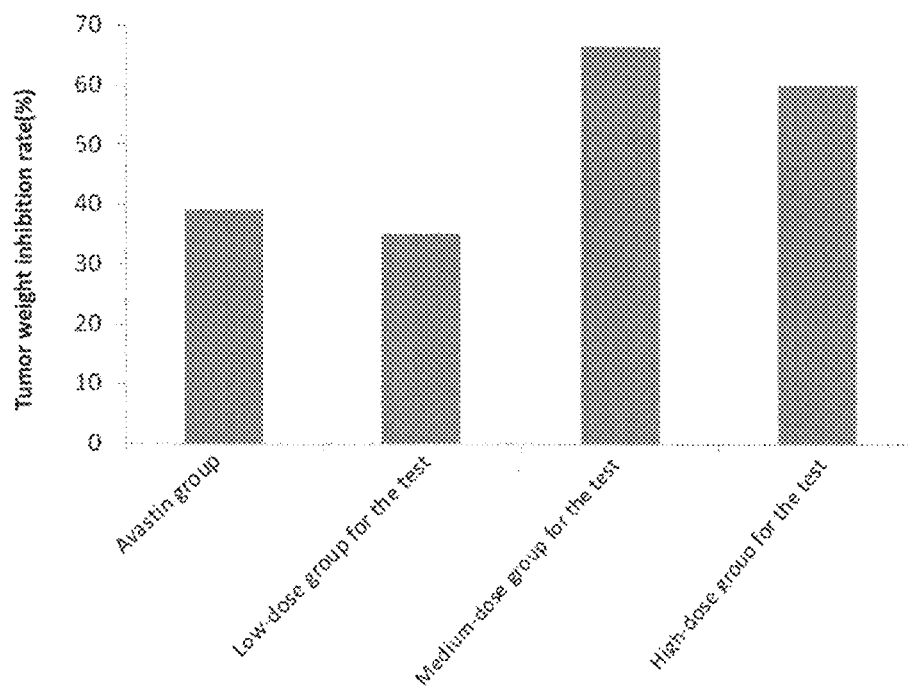

The tumor weight inhibition rate in each group was shown in FIG. 9B: Avastin treatment group has a tumor weight inhibition rate of 38.99%, and the low, medium and high dose groups of the humanized hPV19 antibody treatment have the tumor weight inhibition rates of 35.20%, 66.56%, 59.92%, respectively. These results indicate that humanized hPV19 antibody of the medium and high dose groups can inhibit the tumor growth to a different extent, with the degree of inhibition higher than Avastin of the same dose group.

Example 12

Humanized hPV19 Antibody Inhibiting the Growth of Transplanted Human A673 Rhabdomyosarcoma in Nude Mice Step 1

Establishment of Transplanted Human A673 Rhabdomyosarcoma Model in Nude Mouse

The establishment of this tumor method is basically the same as that in Example 10.

Nude mice were inoculated with human A673 rhabdomyosarcoma. When the tumor volume reached about 50-100 mm$^3$, a screening was done and those mice bearing tumors too small or too large in size were excluded. The selected mice were then randomly divided into different groups for different doses of drugs Step 2

Treatment of the Human A673 Rhabdomyosarcoma by the Humanized PV19 Antibody

Dividing the above nude mice inoculated with the human A673 rhabdomyosarcoma into the following six groups (6 mice/group) for administration, intraperitoneally injecting twice a week successively for 3 weeks, and ending the test on the 22$^{nd}$ day (D22).

Administration Groups are as Follows:
1) high-dose humanized hPV19 antibody group (high-dose group, 10 mg/kg body weight);
2) medium-dose humanized hPV19 antibody group (medium-dose group, 5 mg/kg body weight);
3) low-dose humanized hPV19 antibody group (low-dose group, 2.5 mg/kg body weight);
4) ultralow-dose humanized hPV19 antibody group (ultralow-dose, 0.5 mg/kg body weight);
5) Avastin control group (5 mg/kg body weight); and
6) Saline negative control group.

During the treatment, mice were observed for general clinical symptoms twice a day, and the body weight and tumor diameters were measured twice a week. At the end of experiment, tumors were removed after euthanasia, and the tumor weight were measured. The treatment effect was measured by the ratio of tumor size in the testing group (T) versus the control group (C), i.e. T/C %. If T/C %≤40, and p value<0.05, the treatment was considered to be effective, while taking the tumor weight inhibition rate of greater than 60% as the validity reference index.

Treatment Results:

Effect on Tumor Growth

Figure 10A:
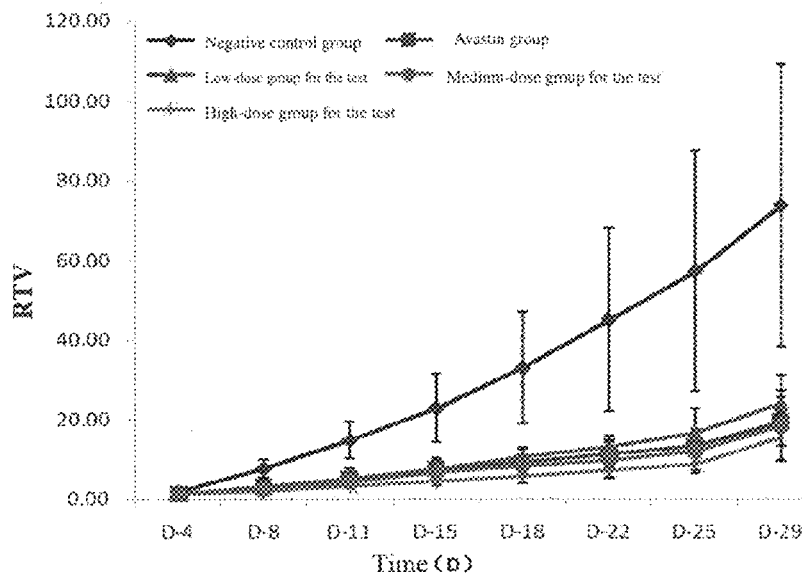

After the first administration, the long and short diameters of the tumor were measured twice a week, and the tumor volume (V) and the relative volume RTV thereof (Vt/VO) were calculated. The relative tumor volume growth trend of A673 tumor in each group was shown in FIG. 10A. As shown in the FIG. 10A, compared with saline negative control group, humanized hPV19 antibody can significantly inhibit the tumor growth.

Effect on Tumor Weight

At day 22, each animal was euthanized, and its tumor was removed and weighted and the average tumor weight in each group was calculated At day 22, each animal was euthanized, and its tumor was removed and weighted and the average tumor weight in each group was calculated.

The negative control group has the average tumor weight of 8.726 g.

The Avastin group has the average tumor weight of 3.323 g, which is significantly less than the negative control group (P≤0.05).

The average tumor weights in the low, medium, high and ultralow dose groups of the humanized hPV19 antibody treatment were 3.811 g, 3.046 g, 2.499 g and 7.056 g, respectively. Compared with the negative control group, the low, medium and high dose groups of humanized HPV19 antibody have a significantly decreased average tumor weight (P≤0.05).

Figure 10B:
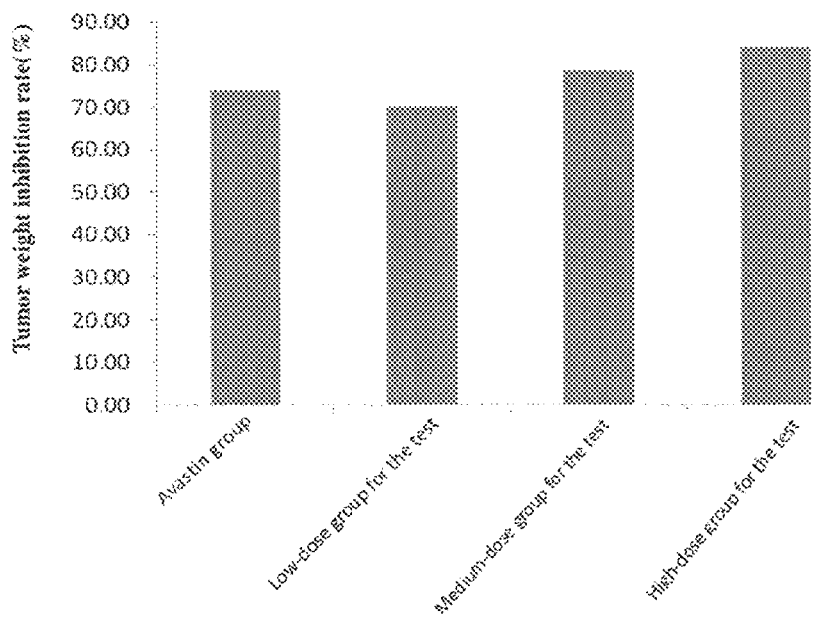

Calculating the tumor weight inhibition rate according to the average tumor weight of each group (FIG. 10B), which shows that the Avastin group has a tumor weight inhibition rate of 61.92%, and the low, medium, high and ultralow dose groups of the humanized HPV19 antibody have the tumor weight inhibition rates of 56.33%, 65.09%, 71.36% and 19.13%, respectively. These results indicate that the humanized hPV19 antibody of the medium and high dose groups can significantly inhibit the tumor growth, with the degree of inhibition as much as Avastin.

Example 13

Humanized hPV19 Antibody Inhibiting the Growth of Transplanted Human HCT-8 Colon Cancer in Nude Mice Step 1

Establishment of Transplanted Human HCT-8 Colon Cancer Model in Nude Mouse

The establishing method is basically the same as that in Example 10.

Observing the tumor growth of the nude mice inoculated with the human HCT-8 colon cancer and, when the tumor volume is about 50-100 mm$^3$, screening according to the size of the tumor volume, with the too large tumor and minor tumor not selected.

Step 2

Treatment of the Human HCT-8 Colon Cancer by Humanized PV19 Antibody

The above nude mice inoculated with human HCT-8 colon cancer were divided into the following seven groups (8 mice/group) for administration, intraperitoneally injecting twice a week successively for 4 weeks, and ending the test on the 30th day (D30).

The treatment grouping is substantially the same as that in Example 9, except the addition of cisplatin chemotherapy drug control group, and an combination treatment group of cisplatin and hPV19 antibody.

The treatment grouping is specifically as follows:
1) high-dose humanized hPV19 antibody group (high-dose group for the test, 10 mg/kg body weight);
2) medium-dose humanized hPV19 antibody group (medium-dose group for the test, 5 mg/kg body weight);
3) low-dose humanized hPV19 antibody group (low-dose group for the test, 2.5 mg/kg body weight);
4) humanized hPV19 antibody ultralow-dose group (ultralow-dose group for the test, 0.5 mg/kg body weight);
5) cisplatin chemotherapy control group (5 mg/kg body weight);
6) combination treatment group (the hPV19 antibody for the test 5 mg/kg+cisplatin 5 mg/kg body weight); and
7) saline negative control group.

During the treatment, mice were observed for general clinical symptoms twice a day, and the body weight and tumor diameters were measured twice a week. At the end of experiment, tumors were removed after euthanasia, and the tumor weight were measured. The treatment effect was measured by the ratio of tumor size in the testing group (T) versus the control group (C), i.e. T/C %. If T/C %≤40, and p value<0.05, the treatment was considered to be effective, while taking the tumor weight inhibition rate of greater than 60% as the validity reference index.

Treatment Results:
Effect on Tumor Growth

Figure 11A:
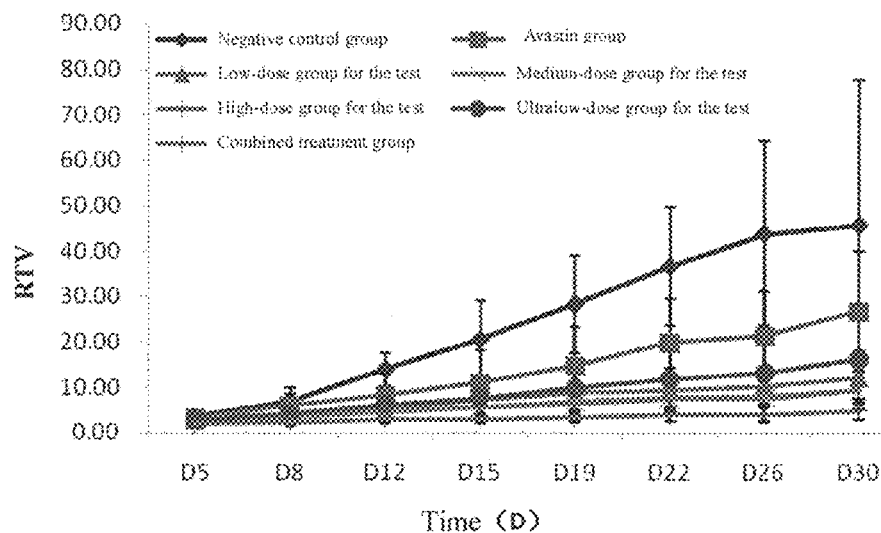

After the first treatment, the long and short diameters of the tumor were measured twice a week, and the tumor volume V and the relative tumor volume RTV thereof (Vt/V0) were calculated The HCT-8 tumor relative volume growth trend of each group was shown in FIG. 11A, the results showed that, compared with the saline negative control group, the humanized HPV19 antibodies of the respective dose groups can inhibit the tumor growth.

Effect on Tumor Weight

At day 30, each animal was euthanized, and its tumor was removed and weighted and the average tumor weight in each group was calculated.

The negative control group has the average tumor weight of 1.608 g.

The average tumor weight of the cisplatin alone group is 1.201 g, which is not significantly different compared to the negative control group.

The low, medium, high and ultralow dose groups of hPV19 monoclonal antibody treatment have the average tumor weights of 0.405 g, 0.278 g, 0.311 g and 0.604 g, respectively, which are significantly less than the negative control group ($P \leq 0.01$ or $P \leq 0.05$); the average tumor weight of hPV19 monoclonal antibody and cisplatin combined treatment group of is 0.193 g, which is significantly less than the negative control group ($P \leq 0.01$).

Figure 11B:
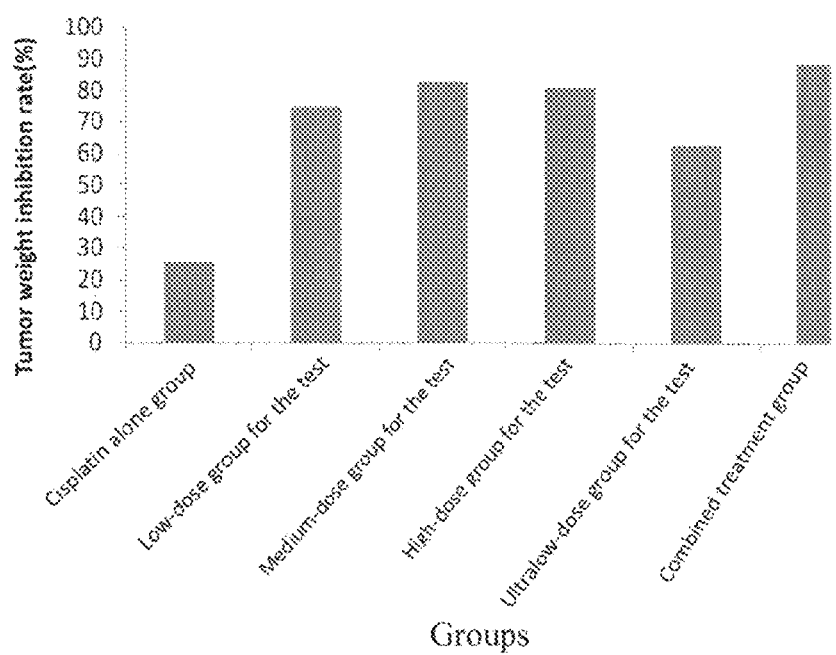

The tumor weight inhibition rate of each group is shown in FIG. 11B. It shows that the tumor weight inhibition rate of cisplatin treatment alone group is 25.29%, and the tumor weight inhibition rates of low, medium, high and ultralow dose groups for the test and the combined treatment group are 74.81%, 82.73%, 80.65%, 62.46% and 87.98%, respectively. These results indicate that humanized hPV19 antibody of each dose group can significantly inhibit the tumor growth, which is still effective even at ultralow dose (0.5 mg/kg). In addition, hPV19 antibody treatment in combination with cisplatin chemotherapy drug is obviously better than either cisplatin treatment (5 mg/kg) alone group or hPV19 antibody treatment (5 mg/kg) alone group.

The present invention provides the gene encoding the variable regions of the heavy-chain and light-chain after protein separation, purification, genetic engineering and other means. Furthermore, the present invention completed humanization of this antibody on the above basis. The DNA fragment encoding the humanized antibody, was inserted into the expression vector (pCDNA3.1), and transferred to Chinese hamster ovary (CHO) cells to obtain recombinant host cell lines. Pure humanized PV19 antibody, with the biological activity of inhibiting tumor growth in vivo, was obtained from cell culture medium by purification. This humanized antibody can be used as a pharmaceutical component, or prepared into a suitable pharmaceutical formulation, used alone or in combination with chemotherapy drugs and other therapies, for treatment in a broad-spectrum of various solid tumors, such as colon cancer, breast cancer and rhabdomyosarcoma.

The invention claimed is:

1. A murine monoclonal antibody that antagonistically inhibits the binding of vascular endothelial growth factor to the receptor thereof, wherein the amino acid sequence of the antibody light-chain variable region is shown by SEQ ID NO:1, and the amino acid sequence of the antibody heavy-chain variable region is shown by SEQ ID NO:2.

2. A DNA molecule or gene encoding the antibody according to claim 1, wherein the nucleic acid sequence of the antibody light-chain variable region is shown by SEQ ID NO:3, and the nucleic acid sequence of the antibody heavy-chain variable region is shown by SEQ ID NO:4.

3. A humanized monoclonal antibody that antagonistically inhibits the binding of vascular endothelial growth factor to the receptor thereof, wherein an antibody heavy-chain variable region and a light-chain variable region of a murine monoclonal antibody that antagonistically inhibits the binding of the vascular endothelial growth factor to the receptor thereof are humanized, with amino acid substitutions of a framework region; and wherein the amino acid sequence of the humanized monoclonal antibody light-chain variable region is shown by SEQ ID NO:5, and the amino acid sequence of the humanized monoclonal antibody heavy-chain variable region is shown by SEQ ID NO:6.

4. A DNA molecule or gene encoding the humanized monoclonal antibody according to claim 3, wherein the nucleic acid sequence of its light-chain variable region is shown by SEQ ID NO:7, and the nucleic acid sequence of its heavy-chain variable region is shown by SEQ ID NO:8.

5. An expression vector comprising the sequence of the DNA molecule according to claim 4 and an expression regulatory sequence in connection with operations of the sequence.

6. A recombinant host cell line, transfected with the expression vector according to claim 5.

7. A pharmaceutical composition comprising a pharmaceutically effective amount of the humanized monoclonal antibody according to claim 3 and a pharmaceutically acceptable vector.

8. A method of treating a disease associated with angiogenesis, the method comprising: administering a pharmaceutical formulation comprising a pharmaceutical composition according to claim 7.

9. The method according to claim 8, wherein the disease is colon cancer, breast cancer or rhabdomyosarcoma.

10. A method of preparing the humanized monoclonal antibody according to claim 3, comprising the following steps:
  a) providing an expression vector, containing a DNA molecule sequence and an expression regulatory sequence in connection with operations of the sequence, the DNA molecule sequence encoding the humanized monoclonal antibody, wherein the nucleic acid sequence of its light-chain variable region is shown by SEQ ID NO:7, and the nucleic acid sequence of its heavy-chain variable region is shown by SEQ ID NO:8 b) transforming a host cell with the expression vector of Step a);

c) culturing the host cell from Step b) under conditions suitable for expression of the humanized monoclonal antibody; and d) separating, purifying and collecting the humanized monoclonal antibody from the host cell culture supernatant.

11. A derivative of a humanized monoclonal antibody, wherein the humanized monoclonal antibody antagonistically inhibits the binding of vascular endothelial growth factor to the receptor thereof, wherein an antibody heavy-chain variable region and a light-chain variable region of a murine monoclonal antibody that antagonistically inhibits the binding of the vascular endothelial growth factor to the receptor thereof are humanized, with amino acid substitutions of a framework region; and wherein the amino acid sequence of the humanized monoclonal antibody light-chain variable region is shown by SEQ ID NO:5, and the amino acid sequence of the humanized monoclonal antibody heavy-chain variable region is shown by SEQ ID NO:6; wherein the amino acid sequences of the antibody light-chain antigen complementarity-determining regions of the derivative are shown by SEQ ID NO:9, SEQ ID NO:10, and SEQ ID NO:11, and the amino acid sequences of the heavy-chain antigen complementarity-determining regions of the derivative are shown by SEQ ID NO:12, SEQ ID NO:13, and SEQ ID NO:14.

12. A pharmaceutical composition comprising a pharmaceutically effective amount of the derivative of the humanized monoclonal antibody according to claim 11 and a pharmaceutically acceptable vector.

13. A method of treating a disease associated with angiogenesis, the method comprising: administering a pharmaceutical formulation comprising a pharmaceutical composition according to claim 12.

14. The method according to claim 13, wherein the disease is colon cancer, breast cancer or rhabdomyosarcoma.

* * * * *

SEQUENCE LISTING

```
<160> NUMBER OF SEQ ID NOS: 21

<210> SEQ ID NO 1
<211> LENGTH: 108
<212> TYPE: PRT
<213> ORGANISM: Mus musculus

<400> SEQUENCE: 1

Asp Ile Val Met Ser Gln Ser Pro Ser Ser Leu Ala Val Ser Ala Gly
1               5                   10                  15

Glu Lys Val Thr Leu Ser Cys Lys Ser Ser Gln Ser Leu Leu Asn Ser
            20                  25                  30

Arg Thr Arg Lys Asn Phe Leu Ala Trp Tyr Gln Gln Lys Pro Gly Gln
```

```
                35                  40                  45
Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Tyr Thr Phe Gly Gly Gly Pro Thr
            100                 105

<210> SEQ ID NO 2
<211> LENGTH: 116
<212> TYPE: PRT
<213> ORGANISM: Mus musculus

<400> SEQUENCE: 2

Gln Pro Gly Gly Ala Phe Trp Met Cys Val Ser Gly Gly Lys Val Thr
1               5                   10                  15

Ile Ser Cys Lys Ala Ser Gly Tyr Ser Phe Thr Asn Ser Gly Ile Asn
                20                  25                  30

Trp Val Lys Gln Ala Pro Gly Lys Gly Leu Lys Trp Met Gly Trp Ile
            35                  40                  45

Asn Thr Tyr Thr Gly Glu Pro Thr Tyr Ala Asp Asp Phe Lys Gly Arg
    50                  55                  60

Phe Ala Phe Ser Leu Glu Thr Ser Ala Ser Ala Tyr Leu Gln Ile
65                  70                  75                  80

Asn Asn Leu Lys Asn Glu Asp Thr Ala Thr Tyr Phe Cys Ala Arg Phe
                85                  90                  95

Gly Asp Gly Tyr Tyr Trp Phe Phe Asp Val Trp Gly Ala Gly Thr Thr
            100                 105                 110

Val Thr Val Ser
        115

<210> SEQ ID NO 3
<211> LENGTH: 324
<212> TYPE: DNA
<213> ORGANISM: Mus musculus

<400> SEQUENCE: 3
gacattgtga tgtcacagtc tccatcctcc ctggctgtgt cagcaggaga gaaggtcact      60
ttgagctgca aatccagtca gagtctgctc aacagtagaa cccgaaaaaa cttcttggct     120
tggtaccagc agaaaccagg gcagtctcct aaactactga tctactgggc atccactagg     180
gaatctgggg tccctgatcg cttcacaggc agtggatctg gacagatttt cactctcacc     240
atcagcagtg tgcaggctga agacctggca gtttattact gcaagcaatc ttataatctg     300
tacacgttcg gcgggggacc aacc                                            324

<210> SEQ ID NO 4
<211> LENGTH: 348
<212> TYPE: DNA
<213> ORGANISM: Mus musculus

<400> SEQUENCE: 4
cagcctgggg gtgccttttg gatgtgtgtt tctggcggga aagtcactat ctcctgcaag      60
gcttctggat attccttcac aaactctgga attaactggg tgaagcaggc tccaggaaag     120
ggtttaaagt ggatgggctg gataaacacc tacactggag agccaacata tgctgatgac     180
```

| | | |
|---|---|---|
| ttcaagggac ggtttgcctt ctctttggaa acctctgcca gctctgccta tttgcagatc | 240 |
| aacaacctca aaaatgagga cacggctaca tatttctgtg caagattcgg agatggttac | 300 |
| tactggttct tcgatgtctg gggcgcaggg accacggtca ccgtctcc | 348 |

<210> SEQ ID NO 5
<211> LENGTH: 113
<212> TYPE: PRT
<213> ORGANISM: Homo sapiens

<400> SEQUENCE: 5

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Phe Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Tyr Thr Phe Gly Gly Gly Thr Asn Leu Glu Ile Lys
            100                 105                 110

Arg

<210> SEQ ID NO 6
<211> LENGTH: 116
<212> TYPE: PRT
<213> ORGANISM: Homo sapiens

<400> SEQUENCE: 6

Asp Val Gln Leu Val Gln Ser Gly Val Glu Val Lys Asn Pro Gly Ala
1               5                   10                  15

Ser Val Lys Val Ser Cys Arg Ala Ser Gly Tyr Ser Phe Thr Asn Ser
            20                  25                  30

Gly Ile Asn Trp Val Lys Gln Ala Pro Gly Lys Gly Leu Lys Trp Met
        35                  40                  45

Gly Trp Ile Asn Thr Tyr Thr Gly Glu Pro Tyr Ala Asp Asp Phe
    50                  55                  60

Lys Gly Arg Phe Ala Phe Ser Leu Glu Thr Ser Ala Ser Ser Ala Tyr
65                  70                  75                  80

Leu Gln Ile Asn Asn Leu Lys Asn Glu Asp Thr Ala Thr Tyr Phe Cys
                85                  90                  95

Ala Arg Phe Gly Asp Gly Tyr Tyr Trp Phe Phe Asp Val Trp Gly Ala
            100                 105                 110

Gly Thr Thr Val
        115

<210> SEQ ID NO 7
<211> LENGTH: 339
<212> TYPE: DNA
<213> ORGANISM: Homo sapiens

<400> SEQUENCE: 7

| | |
|---|---|
| gacatcgtga tgacccagtc tccagactcc ctggctgtgt ctctgggcga gagggccacc | 60 |

```
atcaactgca agtccagcca gagtctgctc aacagtagaa cccgaaaaaa cttcttggct    120
tggtaccagc agaaaccagg gcagtctcct aaactactga tctactgggc atccactagg    180
gaatctgggg tccctgatcg cttcacaggc agtggatctg ggacagattt cactctcacc    240
atcagcagtg tgcaggctga agacctggca gtttattact gcaagcaatc ttataatctg    300
tacacgttcg gcgggggac caacctggaa ataaaacgt                             339
```

<210> SEQ ID NO 8
<211> LENGTH: 357
<212> TYPE: DNA
<213> ORGANISM: Homo sapiens

<400> SEQUENCE: 8

```
gacgtccagc tggtgcagtc tggagttgag gtgaagaacc ctggggcctc agtaaaggtc     60
tcctgcaggg cttctggtta ctccttcaca aactctggaa ttaactgggt gaagcaggct    120
ccaggaaagg gtttaaagtg gatgggctgg ataaacacct acactggaga gccaacatat    180
gctgatgact tcaagggacg gtttgccttc tctttggaaa cctctgccag ctctgcctat    240
ttgcagatca caaacctcaa aaatgaggac acggctacat atttctgtgc aagattcgga    300
gatggttact actggttctt cgatgtctgg ggcgcaggga ccacggtcac cgtctcc      357
```

<210> SEQ ID NO 9
<211> LENGTH: 17
<212> TYPE: PRT
<213> ORGANISM: Mus musculus

<400> SEQUENCE: 9

Lys Ser Ser Gln Ser Leu Leu Asn Ser Arg Thr Arg Lys Asn Phe Leu
1               5                   10                  15

Ala

<210> SEQ ID NO 10
<211> LENGTH: 7
<212> TYPE: PRT
<213> ORGANISM: Mus musculus

<400> SEQUENCE: 10

Trp Ala Ser Thr Arg Glu Ser
1               5

<210> SEQ ID NO 11
<211> LENGTH: 11
<212> TYPE: PRT
<213> ORGANISM: Mus musculus

<400> SEQUENCE: 11

Lys Gln Ser Tyr Asn Leu Tyr Thr Phe Gly Gly
1               5                   10

<210> SEQ ID NO 12
<211> LENGTH: 10
<212> TYPE: PRT
<213> ORGANISM: Mus musculus

<400> SEQUENCE: 12

Gly Tyr Ser Phe Thr Asn Ser Gly Ile Asn
1               5                   10

<210> SEQ ID NO 13

```
<211> LENGTH: 14
<212> TYPE: PRT
<213> ORGANISM: Mus musculus

<400> SEQUENCE: 13

Ile Asn Thr Tyr Thr Gly Glu Pro Thr Tyr Ala Asp Asp Phe
1               5                   10

<210> SEQ ID NO 14
<211> LENGTH: 10
<212> TYPE: PRT
<213> ORGANISM: Mus musculus

<400> SEQUENCE: 14

Phe Gly Asp Gly Tyr Tyr Trp Phe Phe Asp
1               5                   10

<210> SEQ ID NO 15
<211> LENGTH: 20
<212> TYPE: DNA
<213> ORGANISM: Artificial Sequence
<220> FEATURE:
<223> OTHER INFORMATION: Primers
<220> FEATURE:
<221> NAME/KEY: misc_feature
<223> OTHER INFORMATION: Primers

<400> SEQUENCE: 15
tgtcgttcac tgccatcaat                                           20

<210> SEQ ID NO 16
<211> LENGTH: 25
<212> TYPE: DNA
<213> ORGANISM: Artificial Sequence
<220> FEATURE:
<223> OTHER INFORMATION: Primers
<220> FEATURE:
<221> NAME/KEY: misc_feature
<223> OTHER INFORMATION: Primers

<400> SEQUENCE: 16
gacattgtga tgtcacagtc tccat                                     25

<210> SEQ ID NO 17
<211> LENGTH: 28
<212> TYPE: DNA
<213> ORGANISM: Artificial Sequence
<220> FEATURE:
<223> OTHER INFORMATION: Primers
<220> FEATURE:
<221> NAME/KEY: misc_feature
<223> OTHER INFORMATION: Primers

<400> SEQUENCE: 17
aattggatcc agttggtgca gcatcagc                                  28

<210> SEQ ID NO 18
<211> LENGTH: 27
<212> TYPE: DNA
<213> ORGANISM: Artificial Sequence
<220> FEATURE:
<223> OTHER INFORMATION: Primers
<220> FEATURE:
<221> NAME/KEY: misc_feature
<223> OTHER INFORMATION: Primers

<400> SEQUENCE: 18
tcaggccatt acggccmmyc wmaccat                                   27
```

```
<210> SEQ ID NO 19
<211> LENGTH: 28
<212> TYPE: DNA
<213> ORGANISM: Artificial Sequence
<220> FEATURE:
<223> OTHER INFORMATION: Primers
<220> FEATURE:
<221> NAME/KEY: misc_feature
<223> OTHER INFORMATION: Primers

<400> SEQUENCE: 19
aattggatcc tggggtgtc gttttggc                                28

<210> SEQ ID NO 20
<211> LENGTH: 21
<212> TYPE: DNA
<213> ORGANISM: Artificial Sequence
<220> FEATURE:
<223> OTHER INFORMATION: Primers
<220> FEATURE:
<221> NAME/KEY: misc_feature
<223> OTHER INFORMATION: Primers

<400> SEQUENCE: 20
cctcaccaag cccagcacat a                                      21

<210> SEQ ID NO 21
<211> LENGTH: 21
<212> TYPE: DNA
<213> ORGANISM: Artificial Sequence
<220> FEATURE:
<223> OTHER INFORMATION: Primers
<220> FEATURE:
<221> NAME/KEY: misc_feature
<223> OTHER INFORMATION: Primers

<400> SEQUENCE: 21
ctatgtgctg ggcttggtga g                                      21
```